US007585292B2

(12) United States Patent
Anderson et al.

(10) Patent No.: US 7,585,292 B2
(45) Date of Patent: Sep. 8, 2009

(54) MEDICAL SUCTION APPARATUS AND DRAINING OF SAME

(75) Inventors: Barry G. Anderson, Sheboygan, WI (US); Joseph M. Hand, Sheboygan Falls, WI (US)

(73) Assignee: Bemis Manufacturing Company, Sheboygan Falls, WI (US)

( * ) Notice: Subject to any disclaimer, the term of this patent is extended or adjusted under 35 U.S.C. 154(b) by 639 days.

(21) Appl. No.: 10/834,594

(22) Filed: Apr. 29, 2004

(65) Prior Publication Data

US 2004/0204693 A1    Oct. 14, 2004

Related U.S. Application Data

(63) Continuation-in-part of application No. 10/657,432, filed on Sep. 8, 2003, now abandoned.

(60) Provisional application No. 60/192,751, filed on Mar. 28, 2000.

(51) Int. Cl.
*A61M 1/00* (2006.01)

(52) U.S. Cl. .................. 604/322; 604/326; 604/541

(58) Field of Classification Search ................ 604/541, 604/317–326
See application file for complete search history.

(56) References Cited

U.S. PATENT DOCUMENTS

| 1,421,325 A | 6/1922 | Walker et al. |
|---|---|---|
| 1,693,885 A | 12/1928 | Butterworth |
| 1,827,085 A | 10/1931 | Huff |
| 2,004,027 A | 6/1935 | Baxter |
| 2,009,400 A | 7/1935 | Hapgood |
| 2,073,746 A | 3/1937 | Keller |
| 2,208,028 A | 7/1940 | Harrington |
| 2,438,769 A | 3/1948 | Thomas |
| 2,641,270 A | 6/1953 | Allen |
| 2,799,301 A | 7/1957 | Ballard |
| 2,886,071 A | 5/1959 | Rasmussen |
| 3,171,447 A | 3/1965 | Fowler et al. |
| 3,363,627 A | 1/1968 | Bidwell et al. |
| 3,394,831 A | 7/1968 | Bathish et al. |

(Continued)

FOREIGN PATENT DOCUMENTS

EP    0596132 A1    5/1994

(Continued)

OTHER PUBLICATIONS

Med Inc., Medical & Environmental Design, Inc.; Promotional Product Material, Jan. 15, 1991.

*Primary Examiner*—Tatyana Zalukaeva
*Assistant Examiner*—Lynne Anderson
(74) *Attorney, Agent, or Firm*—Michael Best & Friedrich LLP

(57) ABSTRACT

A drainage device and a method for draining a liner-type medical suction apparatus and a rigid-walled container. The drainage device preferably includes a swingarm, a drainhead, and a suction source. The drainhead is positioned to be in fluid communication with the liner-type suction canister or the rigid-walled canister. The swingarm rotates to activate the suction source and inverts the liner-type suction canister or rigid-walled canister. The contents of the canister drain to a sewer system. The method includes the acts of placing the canister on the drainage device, coupling the drainhead to the canister, and activating the suction source.

20 Claims, 18 Drawing Sheets

U.S. PATENT DOCUMENTS

| | | |
|---|---|---|
| 3,482,583 A | 12/1969 | Fenn |
| 3,556,101 A | 1/1971 | Economou |
| 3,603,328 A | 9/1971 | Fenn |
| 3,646,935 A | 3/1972 | Holbrook et al. |
| 3,671,982 A | 6/1972 | Sayles |
| 3,680,560 A | 8/1972 | Pannier, Jr. et al. |
| 3,685,517 A | 8/1972 | Reynolds et al. |
| 3,699,964 A | 10/1972 | Ericson |
| 3,719,197 A | 3/1973 | Pannier, Jr. et al. |
| 3,768,478 A | 10/1973 | Fertik et al. |
| 3,780,757 A | 12/1973 | Jordan |
| 3,782,414 A | 1/1974 | Holbrook |
| 3,791,394 A | 2/1974 | Hammelmann |
| 3,863,664 A | 2/1975 | Holbrook et al. |
| 3,866,608 A | 2/1975 | Reynolds et al. |
| 3,881,486 A | 5/1975 | Fenton |
| 3,897,599 A | 8/1975 | Artzer |
| 3,916,924 A | 11/1975 | McGowan |
| 3,945,392 A | 3/1976 | Deaton et al. |
| 3,958,730 A | 5/1976 | Caldwell |
| 3,989,046 A | 11/1976 | Pannier, Jr. et al. |
| 3,995,333 A | 12/1976 | Stephens |
| 4,004,590 A | 1/1977 | Muriot |
| 4,015,603 A | 4/1977 | Kurtz et al. |
| 4,049,555 A | 9/1977 | Matherne |
| 4,053,284 A | 10/1977 | Posch |
| 4,058,412 A | 11/1977 | Knapp et al. |
| 4,084,723 A | 4/1978 | Parker |
| 4,090,635 A | 5/1978 | Nelson et al. |
| 4,108,336 A | 8/1978 | Anderson, Jr. |
| 4,112,948 A | 9/1978 | Kurtz et al. |
| 4,135,515 A | 1/1979 | Muriot |
| 4,157,718 A | 6/1979 | Baehr |
| 4,195,633 A | 4/1980 | Nehring et al. |
| 4,195,672 A | 4/1980 | Freeman |
| 4,228,798 A | 10/1980 | Deaton |
| 4,238,892 A | 12/1980 | Geiss |
| 4,245,637 A | 1/1981 | Nichols |
| 4,258,824 A | 3/1981 | Kurtz et al. |
| 4,275,732 A | 6/1981 | Gereg |
| 4,306,557 A | 12/1981 | North |
| 4,321,922 A | 3/1982 | Deaton |
| 4,341,568 A | 7/1982 | Christensen |
| 4,345,342 A | 8/1982 | Saito |
| 4,356,084 A | 10/1982 | Hatton et al. |
| 4,363,340 A | 12/1982 | Naftulin |
| 4,384,580 A | 5/1983 | Leviton |
| 4,388,922 A | 6/1983 | Telang |
| 4,429,803 A | 2/1984 | Butterfield |
| 4,430,084 A | 2/1984 | Deaton |
| 4,430,085 A | 2/1984 | Ahrens |
| 4,455,140 A | 6/1984 | Joslin |
| 4,484,920 A | 11/1984 | Kaufman et al. |
| 4,519,427 A | 5/1985 | Ono et al. |
| 4,540,413 A | 9/1985 | Russo |
| 4,559,664 A | 12/1985 | Bohme et al. |
| 4,586,549 A | 5/1986 | White |
| 4,629,159 A | 12/1986 | Wellenstam |
| 4,631,050 A | 12/1986 | Reed et al. |
| 4,666,063 A | 5/1987 | Holoubek et al. |
| 4,673,006 A | 6/1987 | Speck |
| 4,676,281 A | 6/1987 | Nord |
| 4,676,287 A | 6/1987 | Fitzwater |
| 4,681,571 A | 7/1987 | Nehring |
| 4,685,480 A | 8/1987 | Eck |
| 4,698,060 A | 10/1987 | D'Antonio et al. |
| 4,704,106 A | 11/1987 | Shave et al. |
| 4,715,855 A | 12/1987 | D'Antonio et al. |
| 4,735,610 A | 4/1988 | Akkas et al. |
| 4,740,202 A | 4/1988 | Stacey et al. |
| 4,749,010 A | 6/1988 | Petell |
| 4,762,241 A | 8/1988 | Lang |
| 4,770,787 A | 9/1988 | Heath et al. |
| 4,781,707 A | 11/1988 | Boehringer et al. |
| 4,785,963 A | 11/1988 | Magley |
| 4,795,428 A | 1/1989 | Hwang |
| 4,795,448 A | 1/1989 | Stacey et al. |
| 4,808,159 A | 2/1989 | Wilson |
| 4,809,860 A | 3/1989 | Allen |
| 4,813,563 A | 3/1989 | Ogden et al. |
| 4,820,351 A | 4/1989 | Hambleton et al. |
| 4,857,063 A | 8/1989 | Glenn |
| 4,863,446 A | 9/1989 | Parker |
| 4,867,738 A | 9/1989 | Mintz |
| 4,870,975 A | 10/1989 | Cronk et al. |
| 4,889,531 A | 12/1989 | D'Antonio et al. |
| 4,902,284 A | 2/1990 | D'Antonio et al. |
| 4,905,325 A | 3/1990 | Colditz |
| 4,913,179 A | 4/1990 | Engel et al. |
| 4,913,197 A | 4/1990 | Friedrich |
| 4,926,915 A | 5/1990 | Deussen et al. |
| 4,955,874 A | 9/1990 | Farrar et al. |
| 4,957,491 A | 9/1990 | Parker |
| 4,961,440 A | 10/1990 | Wright |
| 4,967,814 A | 11/1990 | Day, Jr. |
| 4,969,491 A | 11/1990 | Kiplinger |
| 4,972,976 A | 11/1990 | Romero |
| 5,011,470 A | 4/1991 | Kurtz et al. |
| 5,024,613 A | 6/1991 | Vasconcellos et al. |
| 5,026,358 A | 6/1991 | Everett, Jr. et al. |
| 5,027,872 A | 7/1991 | Taylor et al. |
| 5,033,492 A | 7/1991 | Mertens et al. |
| 5,045,077 A | 9/1991 | Blake, III |
| 5,049,273 A | 9/1991 | Knox |
| 5,053,026 A | 10/1991 | Andersen et al. |
| 5,064,101 A | 11/1991 | Richter et al. |
| 5,067,950 A | 11/1991 | Broadnax, Jr. |
| 5,071,035 A | 12/1991 | Kiplinger |
| 5,078,677 A | 1/1992 | Gentelia et al. |
| 5,119,830 A | 6/1992 | Davis |
| 5,121,778 A | 6/1992 | Baker et al. |
| 5,154,712 A | 10/1992 | Herweck et al. |
| 5,185,007 A | 2/1993 | Middaugh et al. |
| 5,186,195 A | 2/1993 | Wall |
| 5,192,439 A | 3/1993 | Roth et al. |
| 5,195,994 A | 3/1993 | Dieringer |
| 5,217,038 A | 6/1993 | Pinder |
| 5,222,530 A | 6/1993 | Baker et al. |
| 5,242,434 A | 9/1993 | Terry |
| 5,273,083 A | 12/1993 | Burrows |
| 5,300,050 A | 4/1994 | Everett, Jr. et al. |
| 5,349,995 A | 9/1994 | Perez |
| 5,351,859 A | 10/1994 | Jansen |
| 5,380,289 A | 1/1995 | Hemstreet et al. |
| 5,380,314 A | 1/1995 | Herweck et al. |
| 5,437,836 A | 8/1995 | Yamada |
| 5,439,460 A | 8/1995 | Hoover |
| 5,460,193 A | 10/1995 | Levallois et al. |
| 5,470,324 A | 11/1995 | Cook et al. |
| 5,546,979 A | 8/1996 | Clark, II et al. |
| 5,599,331 A | 2/1997 | Hemstreet et al. |
| 5,620,428 A | 4/1997 | Hand |
| 5,624,417 A | 4/1997 | Cook et al. |
| 5,637,103 A | 6/1997 | Kerwin et al. |
| 5,669,892 A | 9/1997 | Keogh et al. |
| 5,678,564 A | 10/1997 | Lawrence et al. |
| 5,683,371 A | 11/1997 | Hand |
| 5,688,255 A | 11/1997 | Hand |
| 5,725,516 A | 3/1998 | Cook et al. |
| 5,741,237 A | 4/1998 | Walker |
| 5,776,118 A | 7/1998 | Seifert et al. |
| 5,776,260 A | 7/1998 | Dunn et al. |
| 5,807,359 A | 9/1998 | Bemis et al. |
| 5,837,103 A | 11/1998 | Trokhan et al. |

| | | |
|---|---|---|
| 5,871,476 A | 2/1999 | Hand |
| 5,901,717 A | 5/1999 | Dunn et al. |
| 5,931,822 A | 8/1999 | Bemis et al. |
| 5,975,096 A | 11/1999 | Dunn et al. |
| 6,027,490 A | 2/2000 | Radford et al. |
| 6,152,902 A | 11/2000 | Christian et al. |
| 6,244,311 B1 | 6/2001 | Hand et al. |
| 6,263,887 B1 | 7/2001 | Dunn |
| 6,358,232 B1 | 3/2002 | Hand et al. |
| 6,368,310 B1 | 4/2002 | Bemis et al. |
| 6,588,436 B2 | 7/2003 | Dunn et al. |
| 6,626,877 B2 | 9/2003 | Anderson et al. |

FOREIGN PATENT DOCUMENTS

| | | |
|---|---|---|
| WO | WO 8602343 | 4/1986 |

MEDICAL SUCTION APPARATUS AND DRAINING OF SAME

RELATED APPLICATIONS

This patent application is a continuation-in-part of application Ser. No. 10/657,432, filed Sep. 8, 2003 now abandoned, which claimed the benefit of prior application Ser. No. 09/819,243, filed on Mar. 28, 2001, now U.S. Pat. No. 6,626,877, which claimed the benefit of provisional patent Application No. 60/192,751, filed on Mar. 28, 2000.

BACKGROUND OF THE INVENTION

Medical suction systems are used in hospital environments and particularly during various surgical procedures to drain and store bodily fluid from a patient. In general, medical suction systems are used in conjunction with a vacuum source, which enables the bodily fluid to be drained from the patient. Two types of medical suction systems used to contain fluid from a patient include a hard canister type suction canister and a liner-type suction canister.

It has become important in environments such as hospitals to eliminate the handling of and thus reduce personnel exposure to bodily fluids. Hospitals typically dispose of the fluid contained in a medical suction apparatus in various ways. Fluid can be poured from the medical suction apparatus down the hospital sink and into a sewer system, can be incinerated as a liquid or solid, or can be disposed of at an approved hazardous waste site.

SUMMARY OF THE INVENTION

The invention provides methods and apparatus for removing fluids from a medical suction apparatus to eliminate the potential for a person handling the apparatus to come into contact with the fluid.

The invention provides a medical device for draining either a liner-type suction canister or a rigid walled suction canister, both having a cover having therein a port and both containing fluid to be drained. The device comprises a housing, a cover, a support member, and a suction source. The housing is in communication with a sanitary sewer line. The cover includes a passageway and has a first position not engageable with a liner-type or a rigid-walled suction canister and a second position engageable with the liner-type or the rigid walled suction canister. In the second position, the passageway is adapted to be in fluid communication with the port in the cover. The support member supports the liner-type or the rigid-walled suction canister. The suction source is in communication with the passageway and is adapted to drain the fluid contained in the liner-type or the rigid-walled suction canister to a sanitary sewer.

The invention provides a medical device for draining the fluid contained in either a liner-type or a rigid-walled suction canister. The device comprises a movable swingarm and a drainhead. The swingarm is adapted to support either the liner-type or the rigid-walled suction canister. The drainhead includes a passageway and is adapted to engage a liner-type or a rigid-walled suction canister to enable fluid communication between the fluid contained in the liner-type or the rigid-walled suction canister and a sewer line.

The invention provides a medical device for draining fluid contained in a liner-type or a rigid walled suction canister having a cover. The device comprises a housing and a swingarm. The swingarm is coupled to the housing and is movable between a first position and a second position. The swingarm is adapted to support either a liner-type or a rigid-walled suction canister, a first drainhead, and a second drainhead. The first drainhead is adapted to engage a cover of the liner-type suction canister. The second drainhead is adapted to engage a cover of the rigid-walled suction canister. The first and second drainheads include a passageway such that fluid is drained from the liner-type or the rigid-walled suction canister through the passageway and into the housing when the swingarm is in its second position.

The invention provides a method for draining either a liner-type or a rigid-walled suction canister filled with fluid using one device. The method comprises coupling a drainhead on the drainage device to a cover of one of the liner-type suction canister and the rigid-walled suction canister, and activating a suction source to drain the fluid from one of the liner-type suction canister and the rigid-walled suction canister through the drainhead to a sanitary sewer.

The invention provides a method for draining a liner-type or a rigid-walled suction canister filled with fluid using one device. The method comprises placing one of the liner-type suction canister and the rigid-walled suction canister in communication with a device, moving a drainhead on the device and the selected one of the liner-type suction canister and the rigid-walled suction canister relative to one another so as to establish fluid communication between the drainhead and a port on a cover of one of the liner-type suction canister and the rigid-walled suction canister, and activating a suction source to drain the fluid from the selected one of the liner-type suction canister and the rigid-walled suction canister through the drainhead to a sanitary sewer.

The invention provides a method for draining either a liner-type or a rigid-walled suction canister filled with fluid using one device. The method comprises selecting one of the liner-type suction canister and the rigid walled suction canister to be drained, selecting a first drainhead if the liner-type suction canister is to be drained, selecting a second drainhead if the rigid-walled suction canister is to be drained, moving the selected drainhead and the selected suction canister relative to one and then to establish fluid communication between a port on a cover of the selected suction canister and the selected drainhead, and activating a suction source to drain the fluid from the selected suction canister, through the selected drainhead, and to a sanitary sewer.

Other features and advantages of the invention will become apparent to those of ordinary skill in the art upon review of the following description, claims and drawings.

Figure 1:
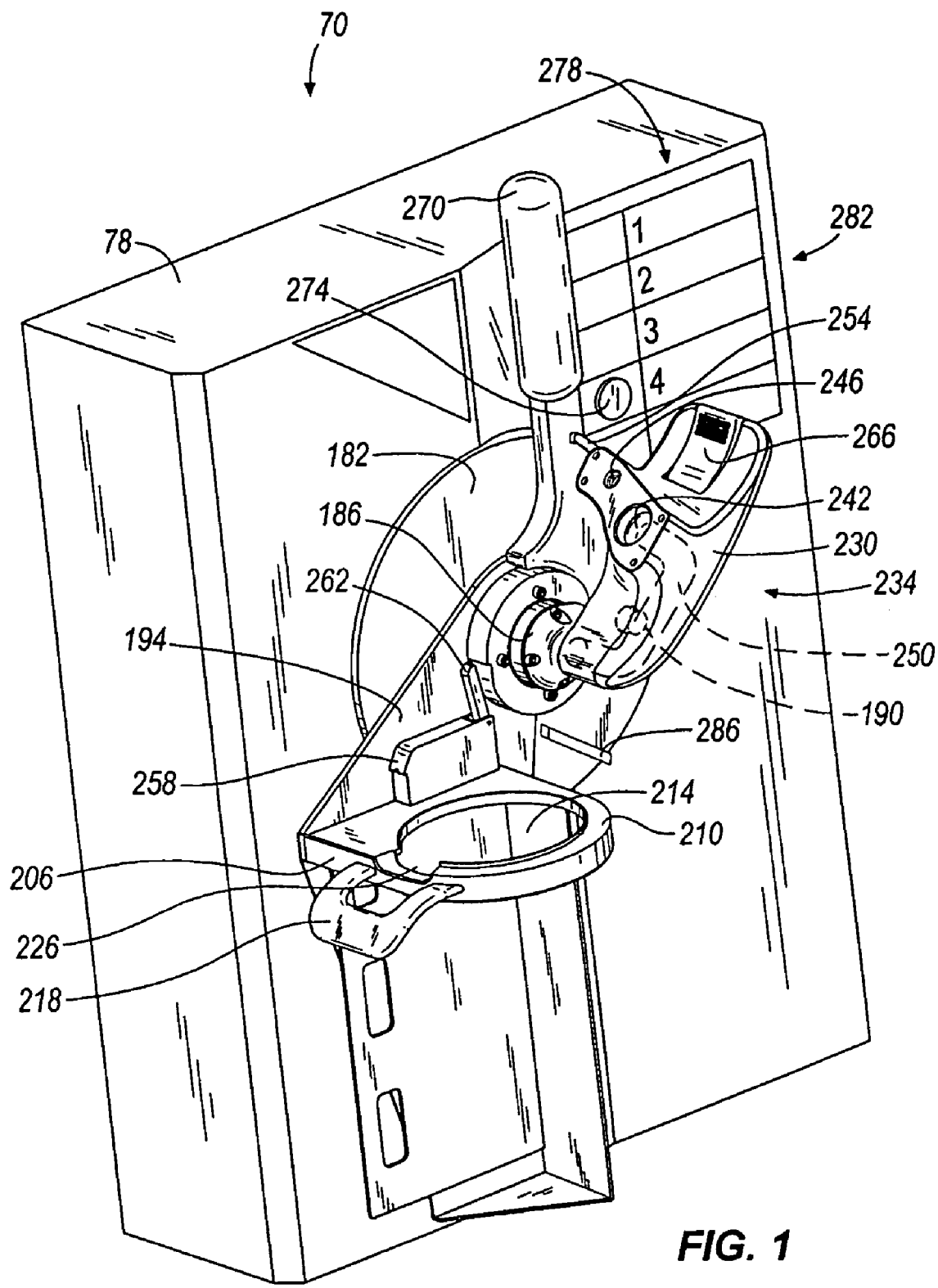
FIG. 1 is a perspective view of an apparatus and a method for draining a liner-type medical suction apparatus and a rigid-walled medical suction apparatus.

Before one embodiment of the invention is explained in detail, it is to be understood that the invention is not limited in its application to the details of construction and the arrangement of components set forth in the following description or illustrated in the drawings. The invention is capable of other embodiments and of being practiced or being carried out in various ways. Also, it is to be understood that the phraseology and terminology used herein is for the purpose of description and should not be regarded as limiting.

DETAILED DESCRIPTION OF THE INVENTION

The entire disclosures of the prior filed applications referenced in the Related Applications section are incorporated herein by reference.

The invention relates to the drainage of liner-type suction canisters and rigid-walled suction canisters. One embodiment of the invention includes a device that is adapted to drain both of the liner-type suction canisters and the rigid-walled suction canisters. In one embodiment, the device includes multiple drainheads that an operator can select depending on whether the liner-type suction canister or the rigid-walled suction canister needs draining. After the appropriate drainhead is selected, it is positioned onto the cover of the suction canister to begin the drainage process. In another embodiment, the covers of the liner-type and rigid-walled suction canisters are compatible such that one drainhead fits on the covers of both types of suction canisters.

Figure 6:
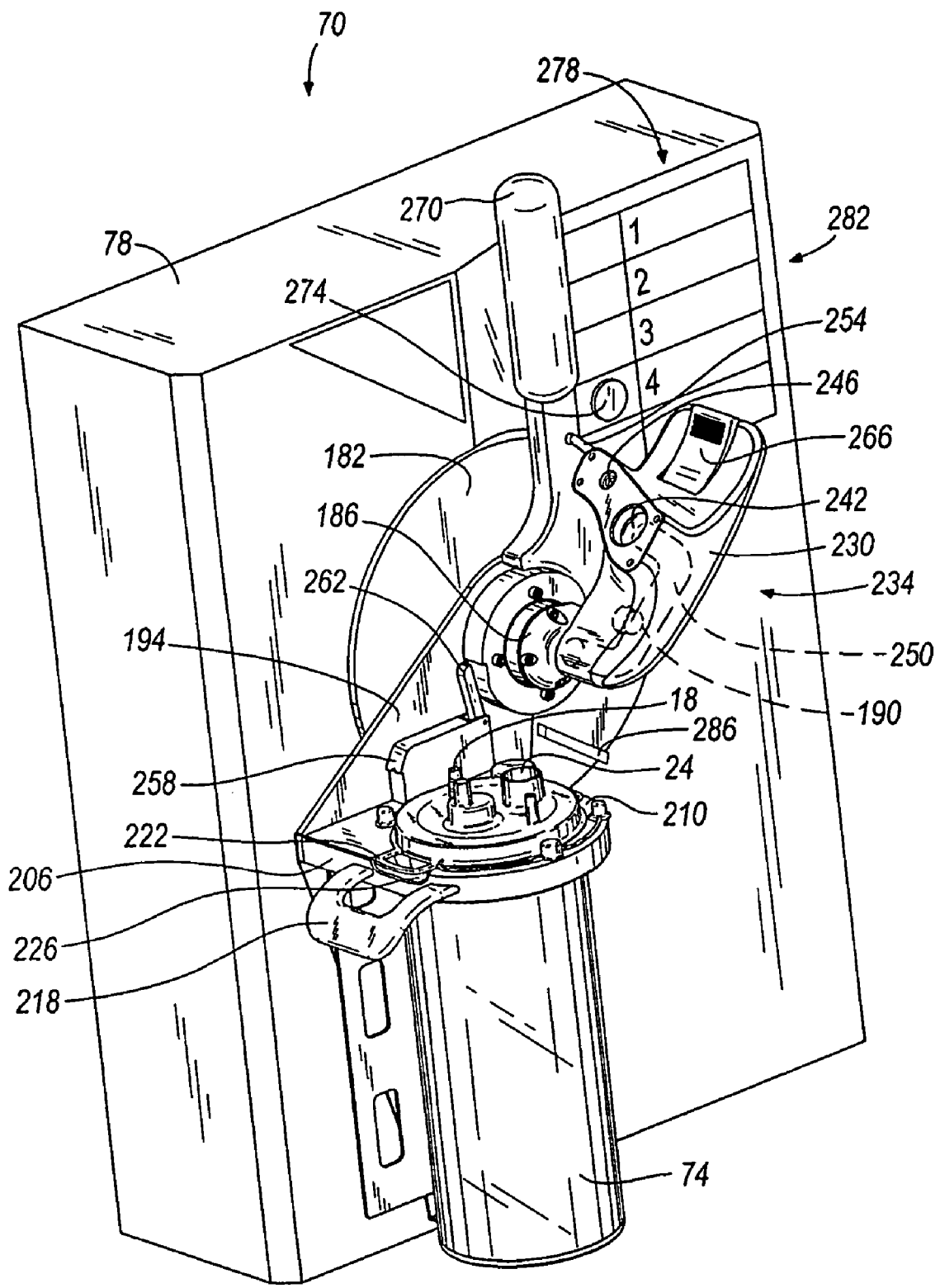
FIG. 6 is a perspective view of the apparatus in FIG. 1 with the rigid-walled medical suction apparatus.
Figure 7:
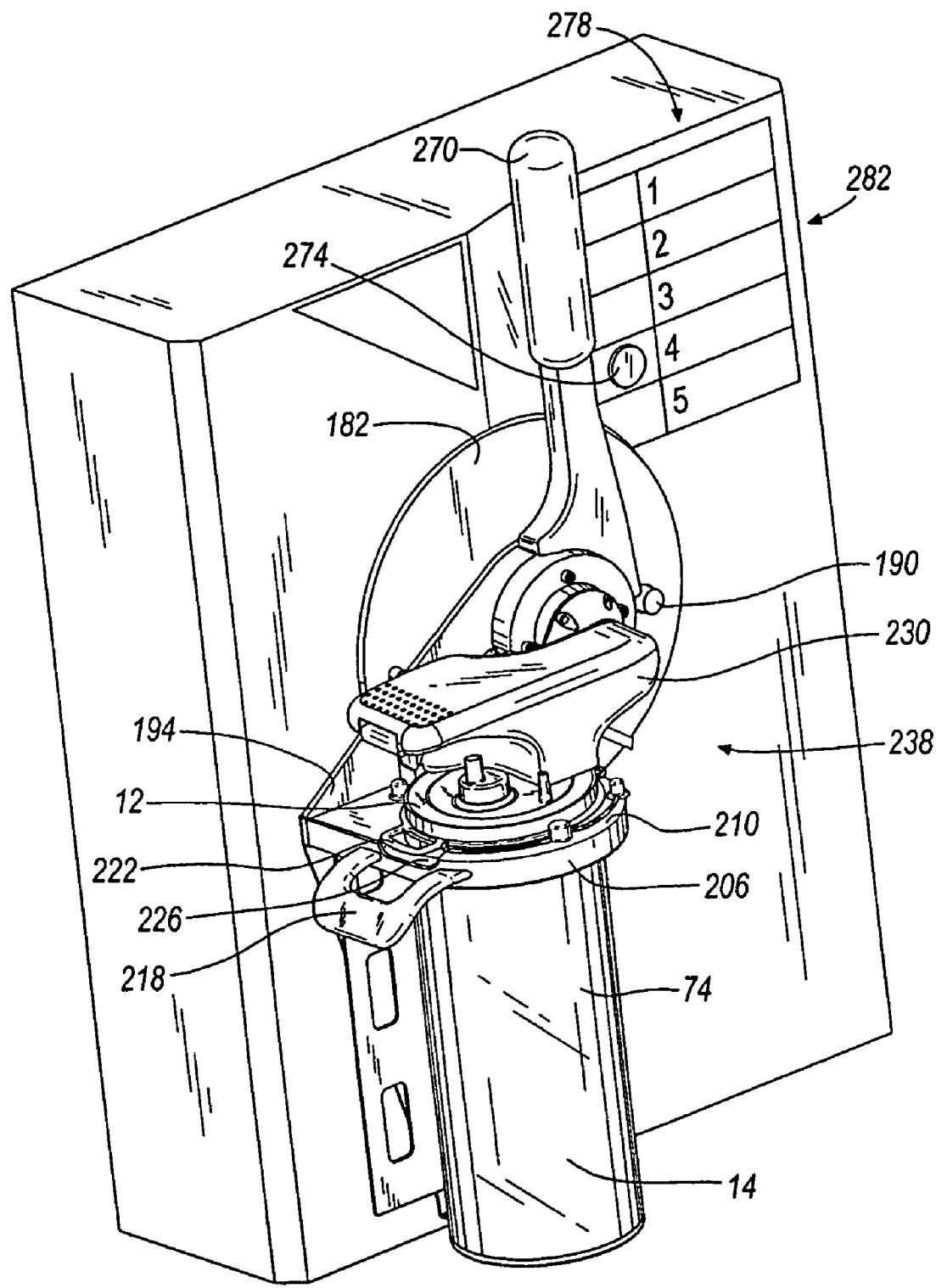
FIG. 7 is a perspective view of the apparatus in FIG. 1 with the rigid-walled medical suction apparatus.
Figure 8:
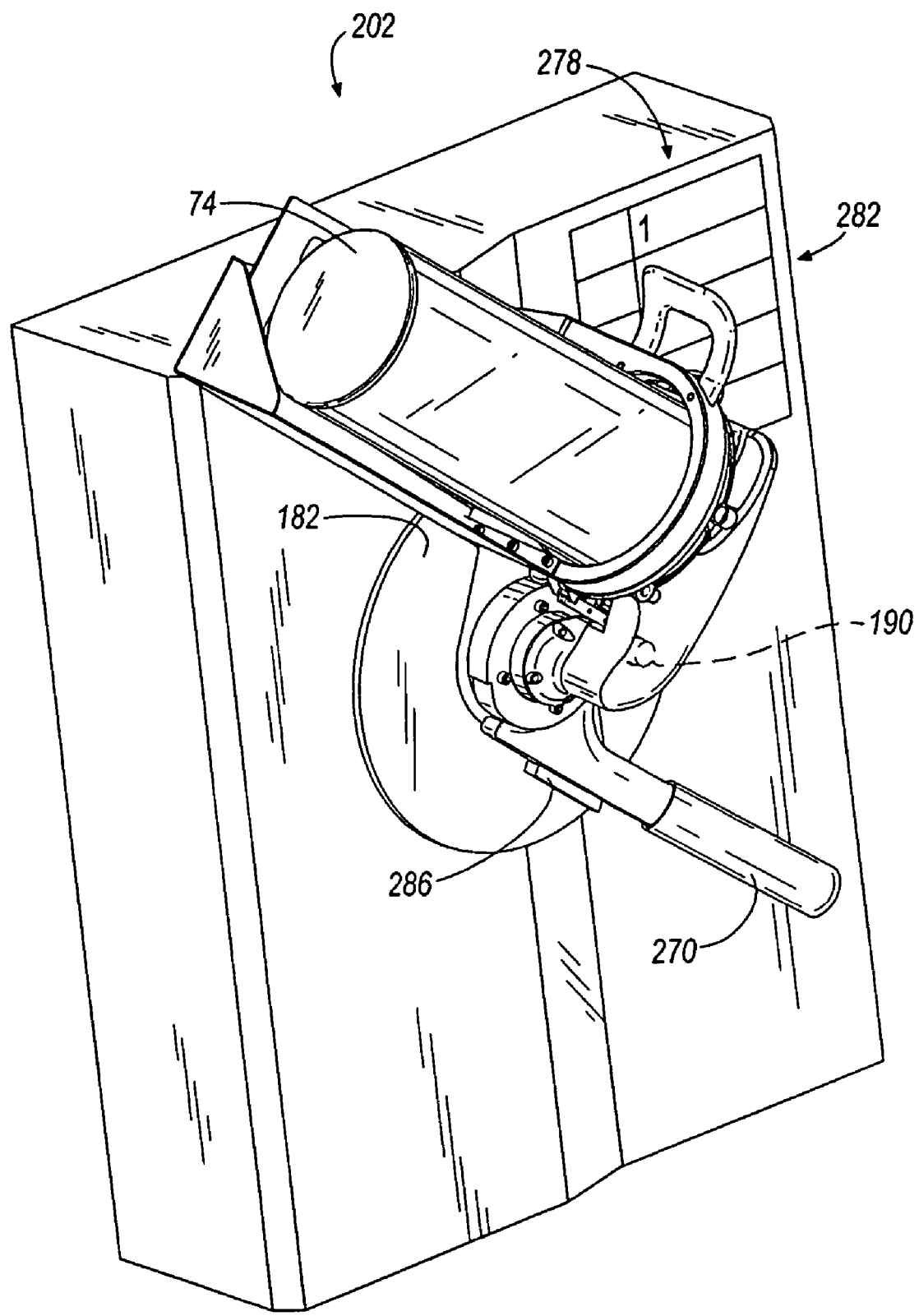
FIG. 8 is a perspective view of the apparatus in FIG. 1 with the rigid-walled medical suction apparatus.
Figure 9:
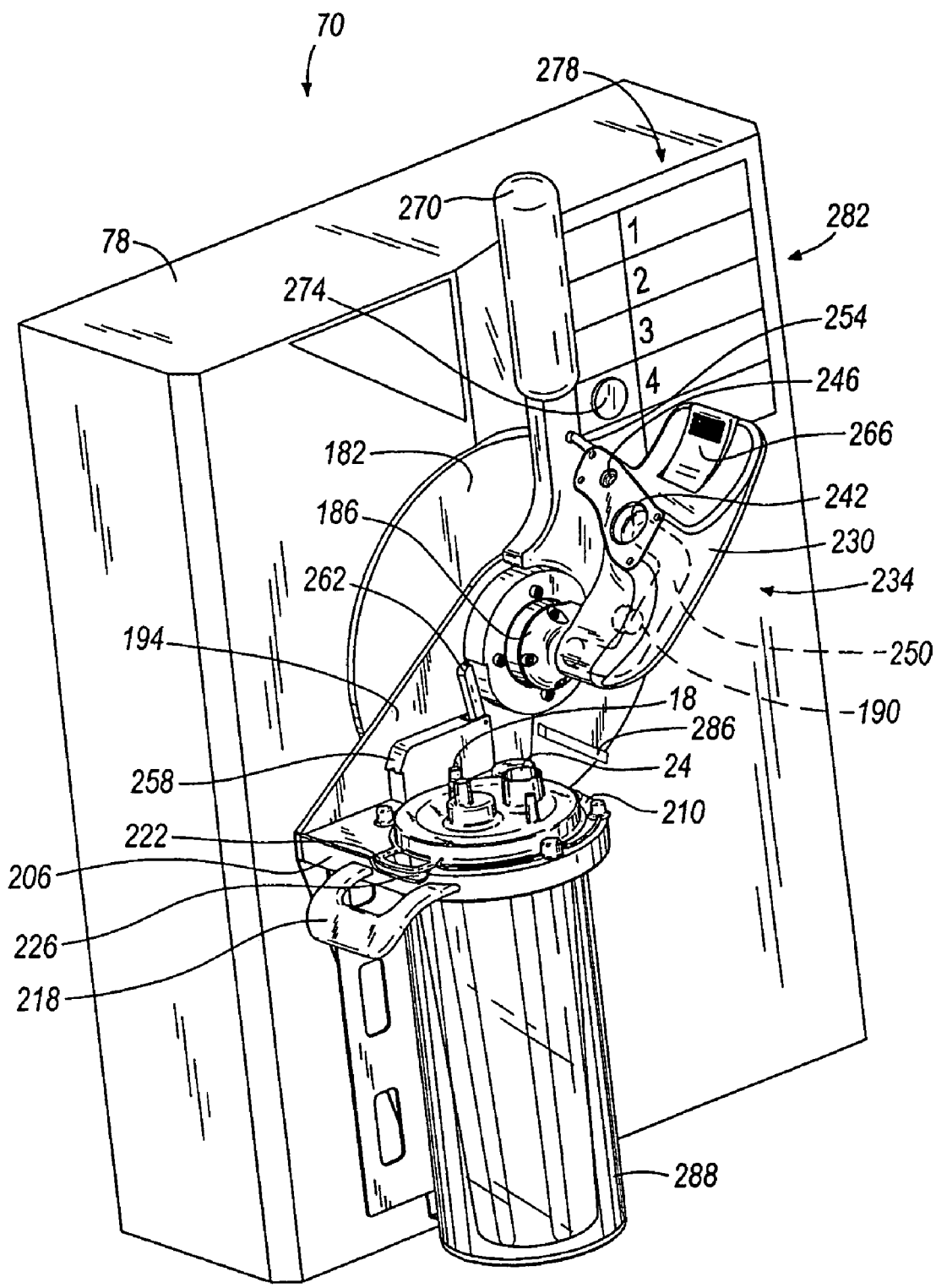
FIG. 9 is a perspective view of the apparatus in FIG. 1 with the liner-type medical suction apparatus and a support container.
Figure 10:
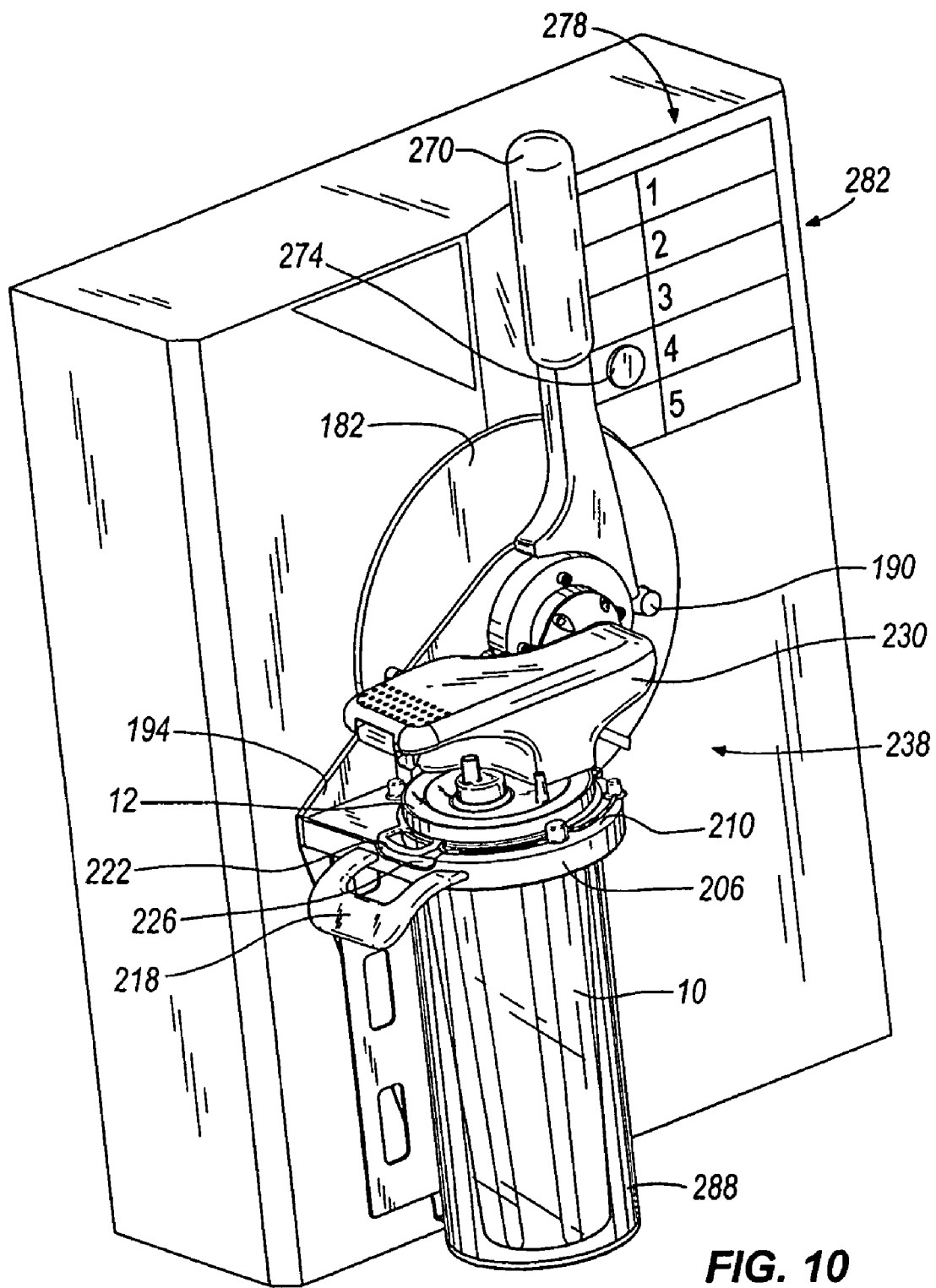
FIG. 10 is a perspective view of the apparatus in FIG. 1 with the liner-type medical suction apparatus and a support container.
Figure 11:
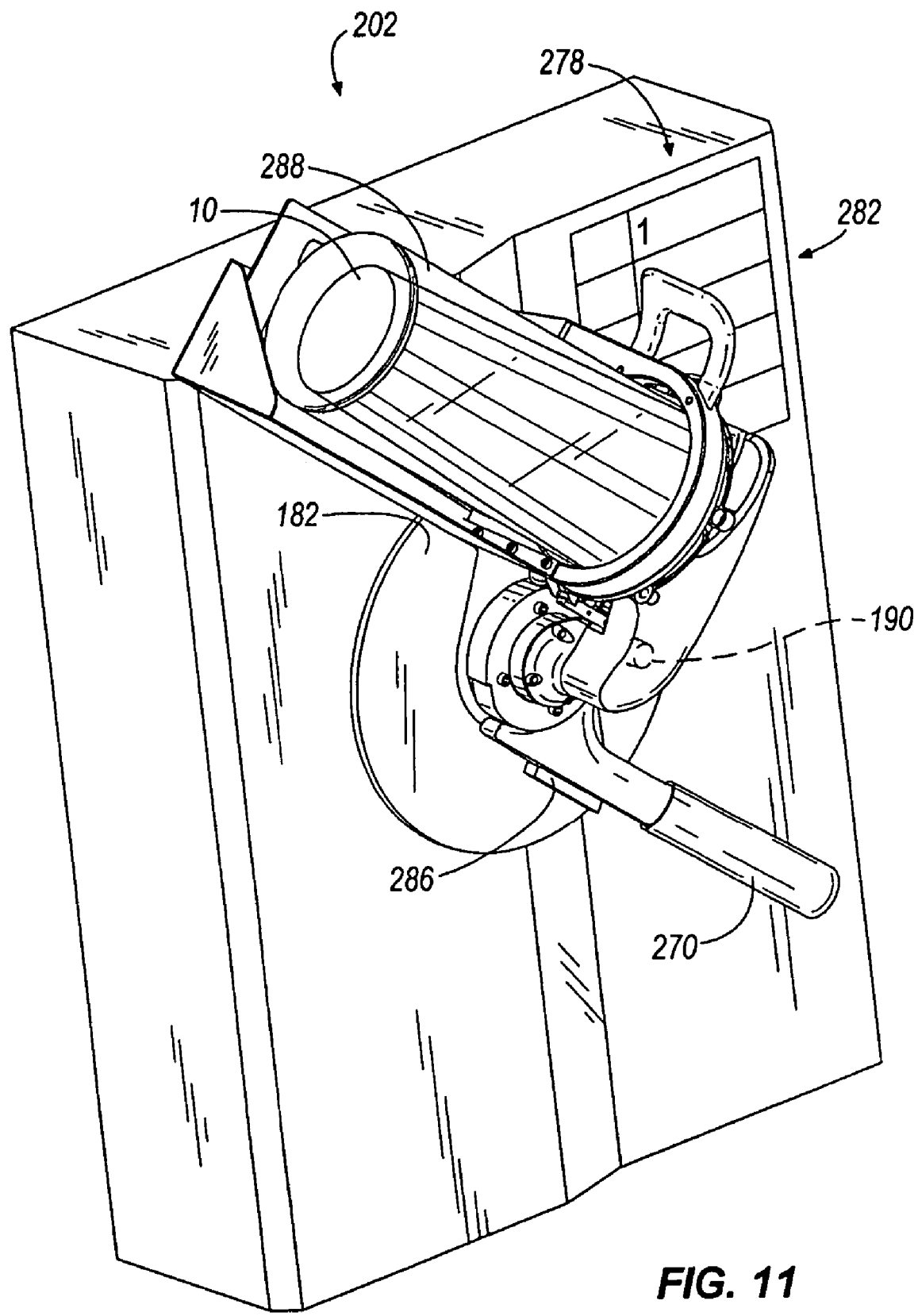
FIG. 11 is a perspective view of the apparatus in FIG. 10 with the liner-type medical suction apparatus and a support container.

FIG. 1 illustrates a drainage device 70 that can be used to drain a liner-type medical suction apparatus 10 (as illustrated in FIGS. 3-5 and 9-11) and a rigid-walled medical suction apparatus 74 (as illustrated in FIG. 6-8). The drainage device 70 can be positioned on the floor (i.e., freestanding) or mounted to a wall.

Figure 2:
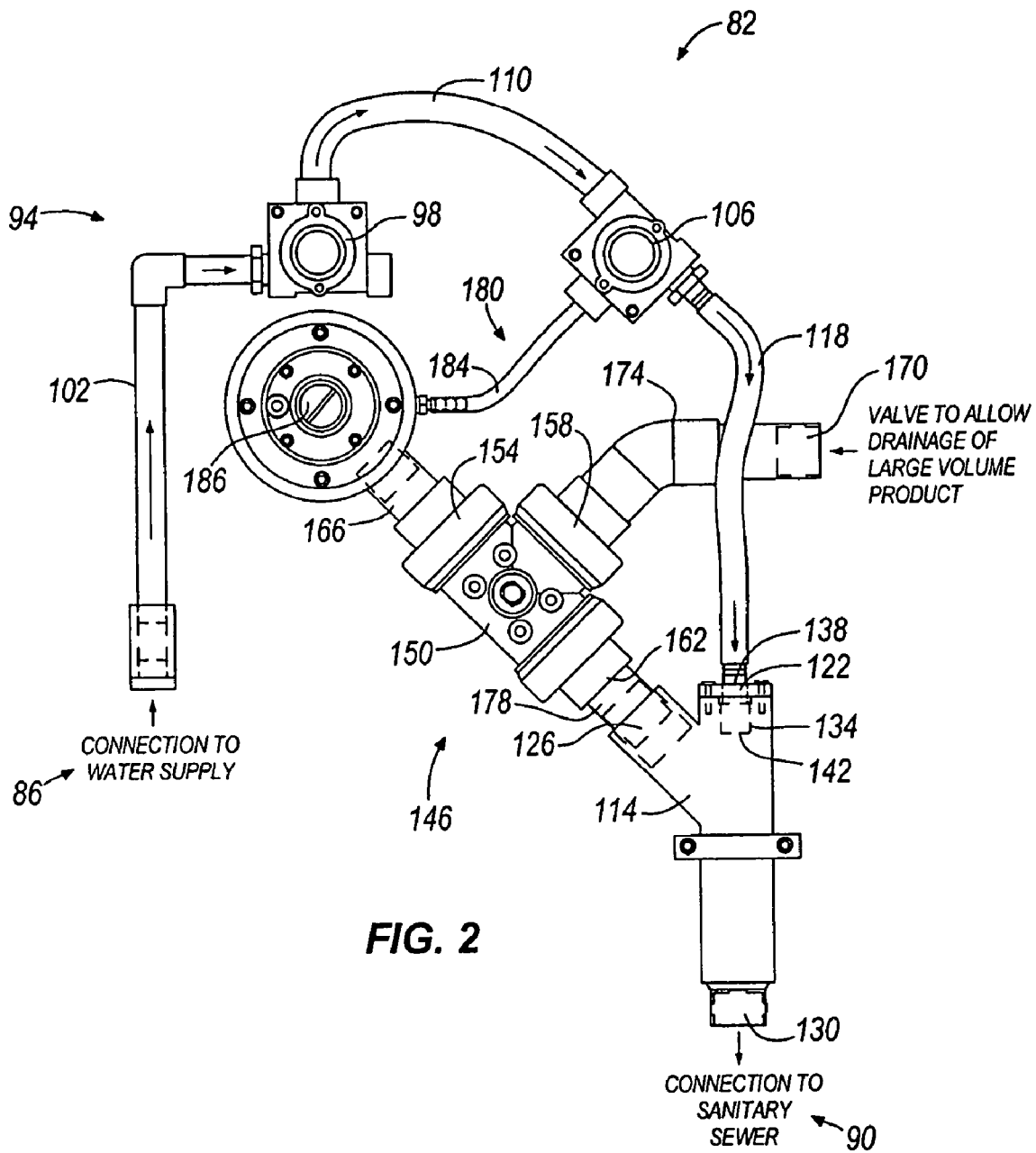
FIG. 2 is a schematic of a plumbing system of the apparatus in FIG. 1.
Figure 3:
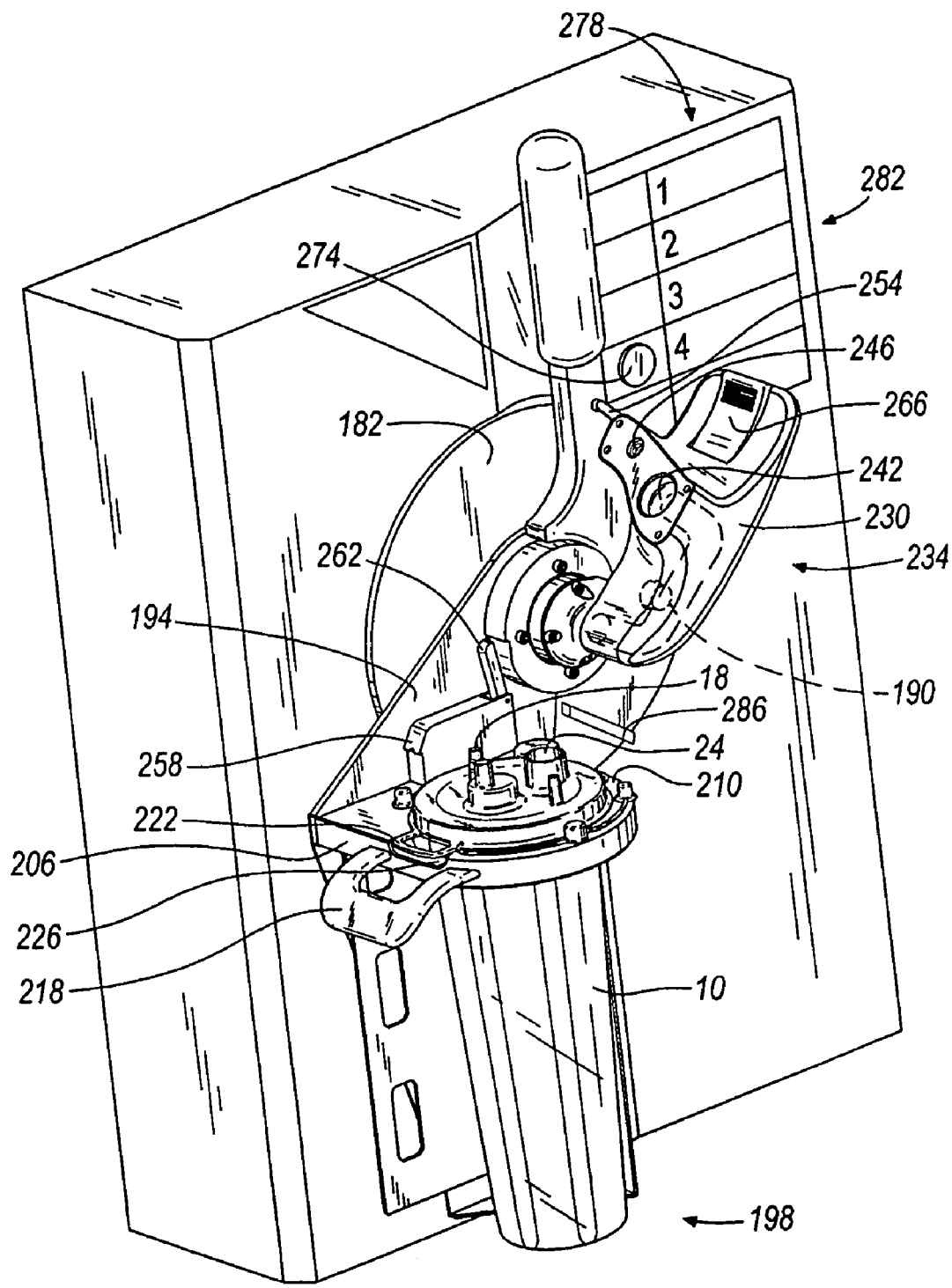
FIG. 3 is a perspective view of the apparatus in FIG. 1 with the liner-type medical suction apparatus.
Figure 4:
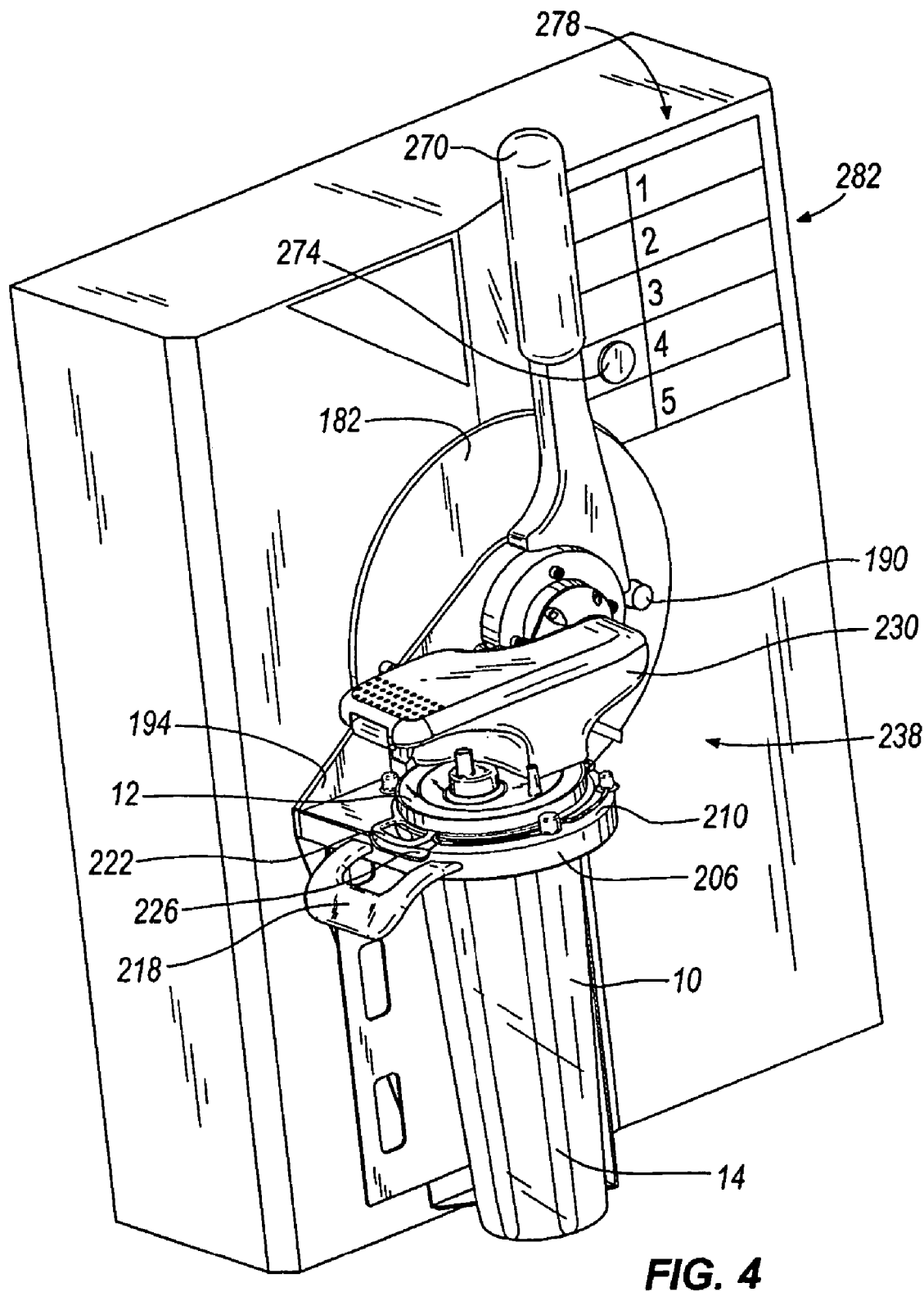
FIG. 4 is a perspective view of the apparatus in FIG. 1 with the liner-type medical suction apparatus.
Figure 5:
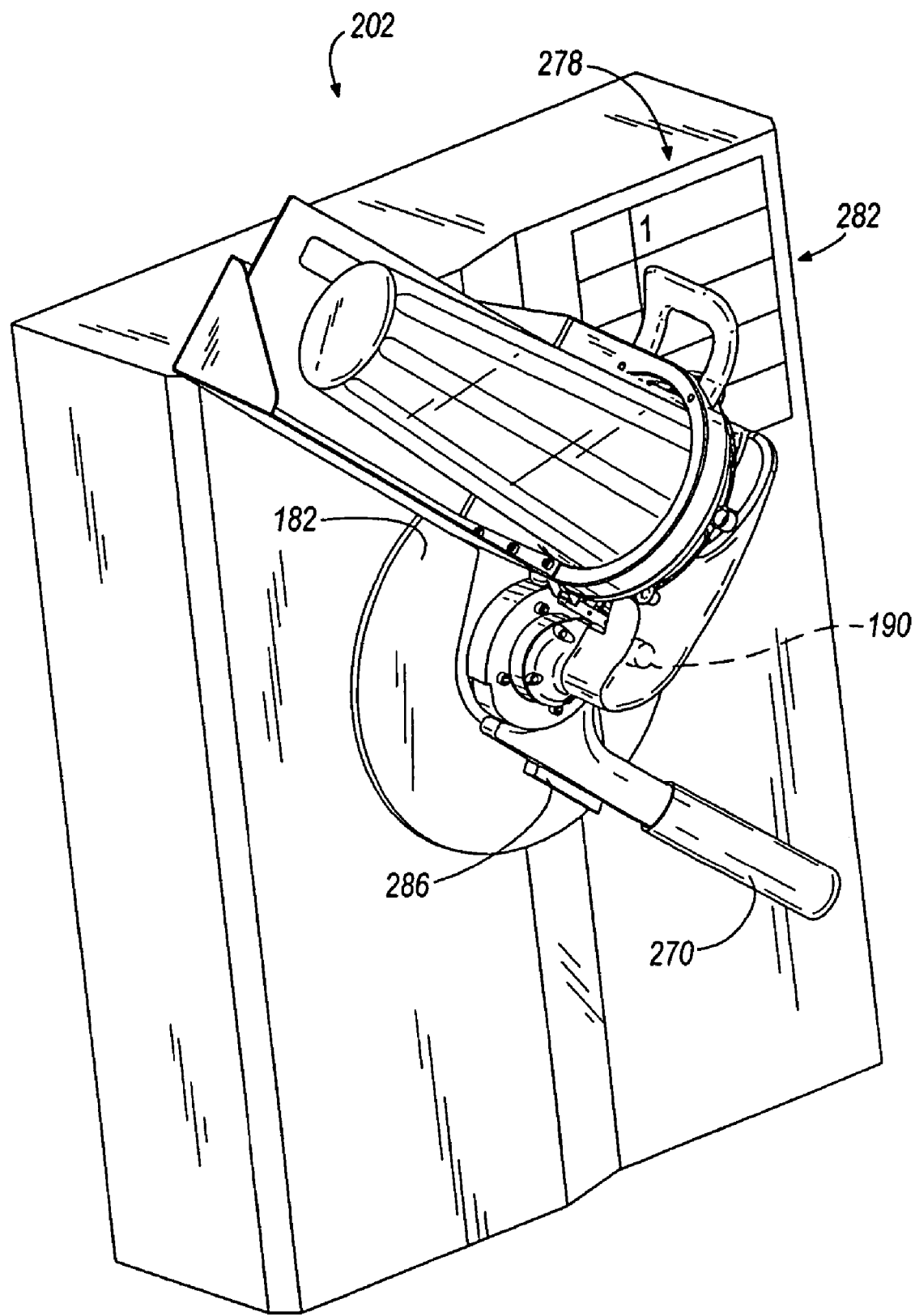
FIG. 5 is a perspective view of the apparatus in FIG. 1 with the liner-type medical suction apparatus.

The drainage device 70 includes a housing 78, which supports a plumbing system 82 (illustrated in FIG. 2). The plumbing system 82 can be supported inside the housing 78 (as illustrated in FIG. 1), outside the housing 78 or partially inside and outside the housing 78. The plumbing system 82 connects to a water supply 86 and sanitary sewer system 90 as illustrated in FIG. 2.

The plumbing system 82 is not limited to the arrangement illustrated in FIG. 2, but rather any number of plumbing systems, components, and/or assemblies, such as conduits, joints, pipes, valves, and the like, can be combined to implement the plumbing system 82, which is within the scope of the invention. FIG. 2 illustrates only one embodiment of the plumbing system 82 utilized with the drainage device 70.

The plumbing system 82 includes a water supply circuit 94, which connects the water supply 86 to the sanitary sewer system 90. The water supply circuit 94 includes a valve 98 and a conduit 102 (or a plurality of conduits that are connectable to form conduit 102) connectable between the water supply 86 and the valve 98. The water supply circuit 94 also includes a spray nozzle valve 106 and a conduit 110 (or a plurality of conduits that are connectable to form conduit 110) connectable between the valve 98 and the valve 106. The water supply circuit 94 further includes a Y-shaped conduit 114 and a conduit 118 (or a plurality of conduits that are connectable to form conduit 118) connectable between the valve 106 and the conduit 114. The conduit 114 includes a first inlet 122, a second inlet 126, and an outlet 130. The outlet 130 of the conduit 114 is connectable to the sanitary sewer system 90. The water supply circuit 94 also includes a suction generator, such as a jet pump 134 positioned in the conduit 114. The jet pump 134 includes a jet pump inlet 138 and a jet pump outlet 142. The jet pump inlet 138 receives the water supplied by the water supply 86 through the conduits 102, 110, and 118 and valves 98 and 106. The jet pump 134 generates a high velocity fluid stream and directs the high velocity fluid stream through the jet pump outlet 142, which generates suction at the second inlet 126 of the conduit 114.

The plumbing system 82 includes a waste flow circuit 146, which connects a drainhead (discussed below) supported on the housing 78 to the sanitary sewer system 90. The waste flow circuit 146 includes a joint conduit 150 having a first inlet 154, a second inlet 158, and an outlet 162. The waste flow circuit 146 also includes a conduit 166 (or a plurality of conduits that are connectable to form conduit 166) connectable to the drainhead (discussed below) and the first inlet 154 of the joint conduit 150. The waste flow circuit 146 further includes a drainage valve 170 and a conduit 174 (or a plurality of conduits that are connectable to form conduit 174) connectable to the valve 170 and the second inlet 158 of the joint conduit 150. The valve 170 can be used to drain larger volumes and/or amounts of product/waste to the sanitary sewer system 90. The waste flow circuit 146 also includes a conduit 178 (or a plurality of conduits that are connectable to form conduit 178) connectable to the outlet 162 of the conduit 150 and the second inlet 126 of the conduit 114.

The plumbing system 82 includes a water spray circuit 180, which connects the water supply 86 to the drainhead (discussed below). The water spray circuit 180 includes a conduit 184 connectable to the valve 106 and the drainhead (discussed below) to allow the flow of water to the interior of the liner-type medical suction apparatus 10 or rigid-walled suction apparatus 74.

Referring back to FIG. 1, the housing 78 includes a stationary disc-like device, such as a wheel 182 supported by a shaft 186. The wheel 182 includes a member 190, which when contacted, activates and/or opens the water valve 98 to start the flow of water from the water supply 86 through the water supply circuit 94.

The housing 78 supports a swingarm 194 as illustrated in FIG. 1. The swingarm 194 is pivotably mounted to the wheel 182 through the shaft 186. The swingarm 194 is pivotally movable between a first position 198 and a second position 202 (illustrated in FIGS. 3-11). In some embodiments of the invention, the second position 202 is in the range of about 90 degrees to about 180 degrees, and more particularly in the range of about 100 degrees to about 140 degrees, and most preferably about 135 degrees, from the first position 198. The swingarm 194 pivots in a preferably clockwise direction when moved between the first position 198 and the second position 202. Likewise, the swingarm 194 rotates in a counter-clockwise direction when moved between the second position 202 and the first position 198. However, movement of the swingarm 194 between positions 198 and 202 can be modified to pivot in varying directions.

The swingarm 194 includes a support member, such as a bracket 206. The bracket 206 supports a flange 210, which is adapted to support either the liner-type medical suction apparatus 10 or the rigid-walled suction apparatus 74. In some embodiments, the flange 210 is removable such that the bracket 206 is adapted to support various sizes of liner-type medical suction apparatuses 10 and rigid-walled suction apparatuses 74. In other embodiments, the bracket 206 is adapted to support various sized flanges 210, which can be exchangeable depending on the size of the liner-type medical suction apparatus 10 and rigid-walled suction apparatus 74. The bracket 206 includes an opening 214 adapted to receive either the liner-type medical suction apparatus 10 or the rigid-walled suction apparatus 74. The bracket 206 can include a handle 218.

The rigid-walled suction apparatus 74 and liner-type medical suction apparatus 10 include an alignment member, such as a notch 222 to be aligned with a recess 226 on the flange 210 or bracket 206 to properly position the liner-type medical suction apparatus 10 and rigid-walled suction apparatus 74 in the bracket 206. Specifically, the notch 222 aligns a cover 12 of the liner-type medical suction apparatus 10 and rigid-walled suction apparatus 74 relative to the drainhead (discussed below). Alternatively, the bracket 206 includes the notch 222 and the liner-type medical suction apparatus 10 and rigid-walled suction apparatus 74 include the recess 226.

The housing 78 supports a drainhead 230 as illustrated in FIG. 1. The drainhead 230 is preferably pivotally mounted to the wheel 182 through the shaft 186. The drainhead 230 is preferably pivotally movable between a first position 234 and a second position 238 (illustrated in FIGS. 4, 7, and 10). In some embodiments of the invention, the second position 238 is in the range of about 90 degrees to about 180 degrees, and more particularly in the range of about 100 degrees to about 140 degrees, and most preferably about 135 degrees, from the first position 234. The drainhead 230 preferably pivots in a counter-clockwise direction when moved between the first position 234 and the second position 238. Likewise, the drainhead 230 rotates in a clockwise direction when moved between the second position 238 and the first position 234. However, movement of the drainhead 230 between positions 234 and 238 can be modified to move in any direction.

As illustrated in FIG. 1, the drainhead 230 includes a drainage port 242 and a spray port 246. The drainage port 242 interengages with the open port 24 on the cover 12 of the liner-type medical suction apparatus 10 or cover 12 of the rigid-walled suction apparatus 74, and the spray port 246 interengages with a patient port 18 on the cover 12, when the drainhead 230 is in the second position 238 (shown in FIGS. 4, 7, and 10). The drainhead 230 can include additional ports to interengage with other ports on the cover 12. The drainhead 230 includes a passageway 250 adapted to be in fluid communication with the open port 24 on the cover 12 and the conduit 166.

The drainhead 230 includes a latch 254 that engages a swingarm lock 258, which is supported on the swingarm 194. The swingarm 194 also includes an interlock 262 that is released when the latch 254 engages the swingarm lock 258. The swingarm interlock 262 is positioned in such a manner to prevent the swingarm 194 from rotating without properly securing the drainhead 230 to the cover 12 of the liner-type medical suction apparatus 10 or cover 12 of the rigid-walled suction apparatus 74. With the interlock 262 released, the swingarm 194 is pivotably movable.

The drainhead 230 includes a lever 266, which, when activated or depressed, releases the drainhead latch 254 so the drainhead 230 can be moved from the second position 238 to the first position 234.

In some embodiments, the drainhead 230 is removable from the wheel 182 and exchanged with a different oriented drainhead 230 to accommodate various arrangements and sizes of ports on different covers 12 of the liner-type and rigid-walled suction apparatuses 10 and 74. The drainhead 230 can be color-coded or otherwise marked to indicate the liner-type medical suction apparatus 10 and/or rigid-walled suction apparatus 74 the drainhead will fit.

In other embodiments, the drainhead 230 can include multiple drainage ports and spray ports that accommodate various arrangements and sizes of ports on different covers 12 of the liner-type and rigid-walled suction apparatuses 10 and 74. The drainhead 230 can be swivelable such that an operator can select the appropriate drainage port and/or spray port for the cover 12 of the liner-type medical suction apparatus 10 or rigid-walled suction apparatus 74 being drained.

The swingarm 194 includes a handle 270 as illustrated in FIG. 1. The handle 270 is pivotably mounted to the wheel 182 through the shaft 186. The handle 270 is engaged by the operator of the drainage device 70 and facilitates movement of the swingarm 194 between the first position 234 and the second position 238 (illustrated in FIGS. 3-11). As the swingarm 194 is rotated, the swingarm 194 contacts the member 190, which activates and/or opens the water valve 98 to start the flow of water from the water supply 86 through the water supply circuit 94. Alternatively, the operator can engage the handle 218 to move the swingarm 194 between the first position 234 and the second position 238.

The housing 78 includes a member, such as a button 274 to activate the valve 106 to allow the flow of water to enter the water spray circuit 180, through the drainhead 230, and into the interior of the liner-type medical suction apparatus 10 and or rigid-walled suction apparatus 74. The button 274 can be positioned anywhere on the housing 78.

The housing 78 also includes an indicator panel 278 to indicate to the operator the current step in the drainage process. The indicator panel 278 includes multiple indicators 282 that correspond to the steps in the drainage process. For example, the indicators 282 can include one or more of the following and are not limited to, position and align the liner and/or rigid-walled canister in the bracket 206 and/or flange 210; select proper drainhead 230 for liner-type medical suction apparatus 10 and rigid-walled suction apparatus 74; secure the drainhead 230 to the cover 12 of the liner-type medical suction apparatus 10 or the rigid-walled suction apparatus 74; rotate swingarm 194 (with or without use of the handle 270); rinse the liner-type medical suction apparatus 10 or the rigid-walled suction apparatus 74; rotate swingarm 194 to original position; release the drainhead 230; remove liner-type medical suction apparatus 10 or the rigid-walled suction apparatus 74. The indicator panel 278 can include light emitting diodes or other indication devices to illuminate and identify the current step in the drainage process. The drainage device 70 includes intelligent software and sensors to detect, but is not limited to, whether the liner-type medical suction apparatus 10 or the rigid-walled suction apparatus 74 are positioned and aligned in the bracket 206 and/or flange 210, whether the drainhead 230 is locked in the second position 238, when the liner-type medical suction apparatus 10 or the rigid-walled suction apparatus 74 has been drained, whether the swingarm 194 has been returned to the first position 198, and when the drainhead 230 has been released. Alternatively, various parts of the drainage device 70 can be color-coded to correspond to the color-coded section in the indicator panel 278 to provide instructions to the operator.

The drainage device 70 operates to drain the contents of the liner-type medical suction apparatus 10 and/or the rigid-walled suction apparatus 74 in a manner in which there is minimal and preferably no contact with the liner or canister contents. Throughout the drainage process, the indicator panel 278 illuminates the indicator 282 to inform the operator of the current step in the process. An operator determines whether a flange 210 is needed, selects the appropriate flange 210 if needed, positions the liner-type medical suction apparatus 10 or the rigid-walled suction apparatus 74 (in need of emptying or draining) in the bracket 206 with or without the flange 210, and aligns the notch 222 on the liner-type medical suction apparatus 10 or the rigid-walled suction apparatus 74 with the recess 226 on the bracket 206. In some embodiments, the liner-type medical suction apparatus 10 can be supported by a container 288 for drainage, whereby the operator inserts the liner-type medical suction apparatus 10 into the container 288 and presses the cover 12 onto the flange 210 to create an airtight seal within the container 288. The airtight seal keeps the liner 14 expanded during the drainage process to allow for more complete drainage of the liner 14.

The operator removes any caps or like devices from the patient port 18 and an open port 24 on the cover 12. Next, the operator selects the appropriately sized drainhead 230 (if necessary) and moves the drainhead 230 from its first position 234 to its second position 238 (illustrated in FIGS. 3-11) such that the latch 254 engages the swingarm lock 258 to release the swingarm interlock 262.

The operator engages the handle 270 and/or the bracket handle 218 to move the swingarm 194 from the first position 198 to the second position 202 (illustrated in FIGS. 3-11). As the swingarm 194 is moved (and generally before the swingarm reaches the second position 202), the swingarm 194 contacts the member 190, which activates and/or opens the valve 98 to start the flow of water from the water supply 86 through the water supply circuit 94. The swingarm 194 is moved clockwise (about 135 degrees) until the handle 270 makes contact with a stop 286 (illustrated in FIGS. 3-11) supported by the wheel 182.

The flow of water through the water supply circuit 94 and jet pump 134 generates suction at the second inlet 126 of the conduit 114 and in the interior of the liner-type medical suction apparatus 10 or the rigid-walled suction apparatus 74. The suction along with gravity facilitate drainage of the contents of the liner-type medical suction apparatus 10 or the rigid-walled suction apparatus 74. The contents travel through the waste flow circuit 146 to the sanitary sewer system 90.

After drainage of the liner-type medical suction apparatus 10 or the rigid-walled suction apparatus 74 is completed, the operator can optionally activate the button 274, which allows water to enter the water spray circuit 180, through the drainhead 230, spray port 246, patient port 18, and into the interior of the liner-type medical suction apparatus 10 or the rigid-walled suction apparatus 74. The water is sprayed into the liner-type medical suction apparatus 10 or the rigid-walled suction apparatus 74 to clean/rinse the interior.

After completion, the operator engages the handle 270 and moves the swingarm 194 from the second position 202 to the first position 198. The operator then depresses the lever 266 on the drainhead 230 to release the latch 254, and moves the drainhead 230 from the second position 238 to the first position 234. The operator can remove either the liner-type medical suction apparatus 10 or the rigid-walled suction apparatus 74 and dispose of it into a white bag medical waste container.

Figure 12:
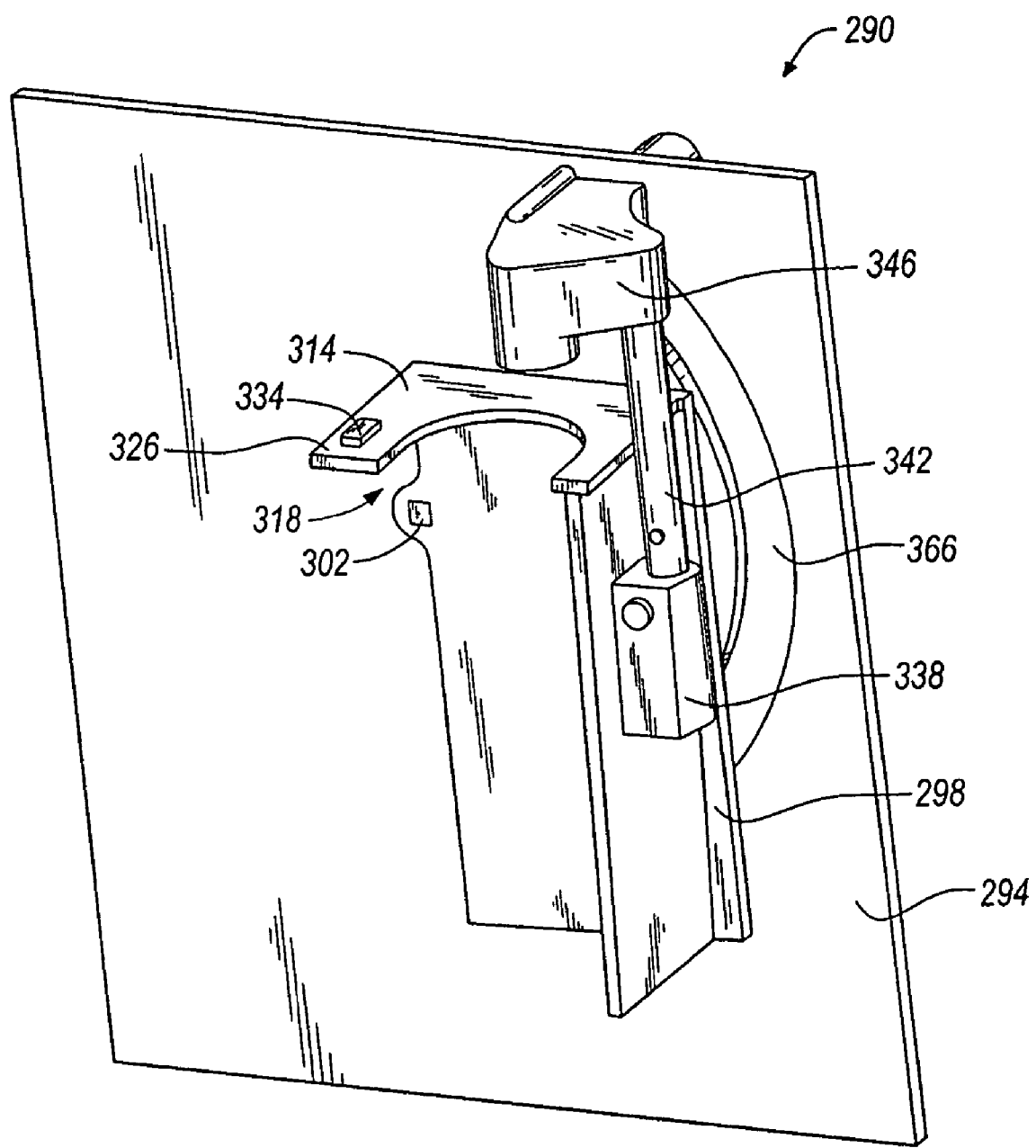
FIG. 12 is a perspective view of an apparatus and a method for draining a liner-type medical suction apparatus and a rigid-walled medical suction apparatus.

FIG. 12 illustrates a drainage device 290 that can be used to drain either a liner-type medical suction apparatus 10 or a rigid-walled suction apparatus 74. The drainage device 290 can be positioned on the floor (i.e., freestanding) or mounted to a wall. The drainage device 290 is illustrated and described with the liner-type medical suction apparatus 10 for ease of description. The drainage device 290 is not illustrated with the or rigid-walled suction apparatus 74, but it is understood that a or rigid-walled suction apparatus 74 can be similarly drained as described herein and as explained above with the drainage device 70.

The drainage device 290 includes a housing 294, which supports a swingarm 298 as illustrated in FIG. 12. The swingarm 298 is pivotably mounted to the housing 294 through a shaft at pivot point 302. The swingarm 298 is pivotably movable from a first position 306 (illustrated in FIG. 13) to a second position 310 (illustrated in FIG. 17).

In some embodiments of the invention, the second position 310 is in the range of about 90 degrees to about 180 degrees, and more particularly in the range of about 100 degrees to about 140 degrees, and most preferably about 135 degrees, from the first position 306. The swingarm 298 pivots in a clockwise direction when moved between the first position 306 and the second position 310. Likewise, the swingarm 298 rotates in a counter-clockwise direction when moved between the second position 310 and the first position 306. However, movement of the swingarm 298 can be modified to vary in the type and direction of movement.

The swingarm 298 includes a support member, such as a bracket 314. The bracket 314 can support a flange, which is adapted to support the liner-type medical suction apparatus 10. In some embodiments, the flange is removable such that the bracket 314 is adapted to support various sizes of liner-type medical suction apparatuses 10. In other embodiments, the bracket 314 is adapted to support various sized flanges, which can be exchangeable depending on the size of the liner-type medical suction apparatus 10. The bracket 314 includes an opening 318 adapted to receive the liner-type medical suction apparatus 10. The bracket 314 can include a handle 326.

Figure 13:
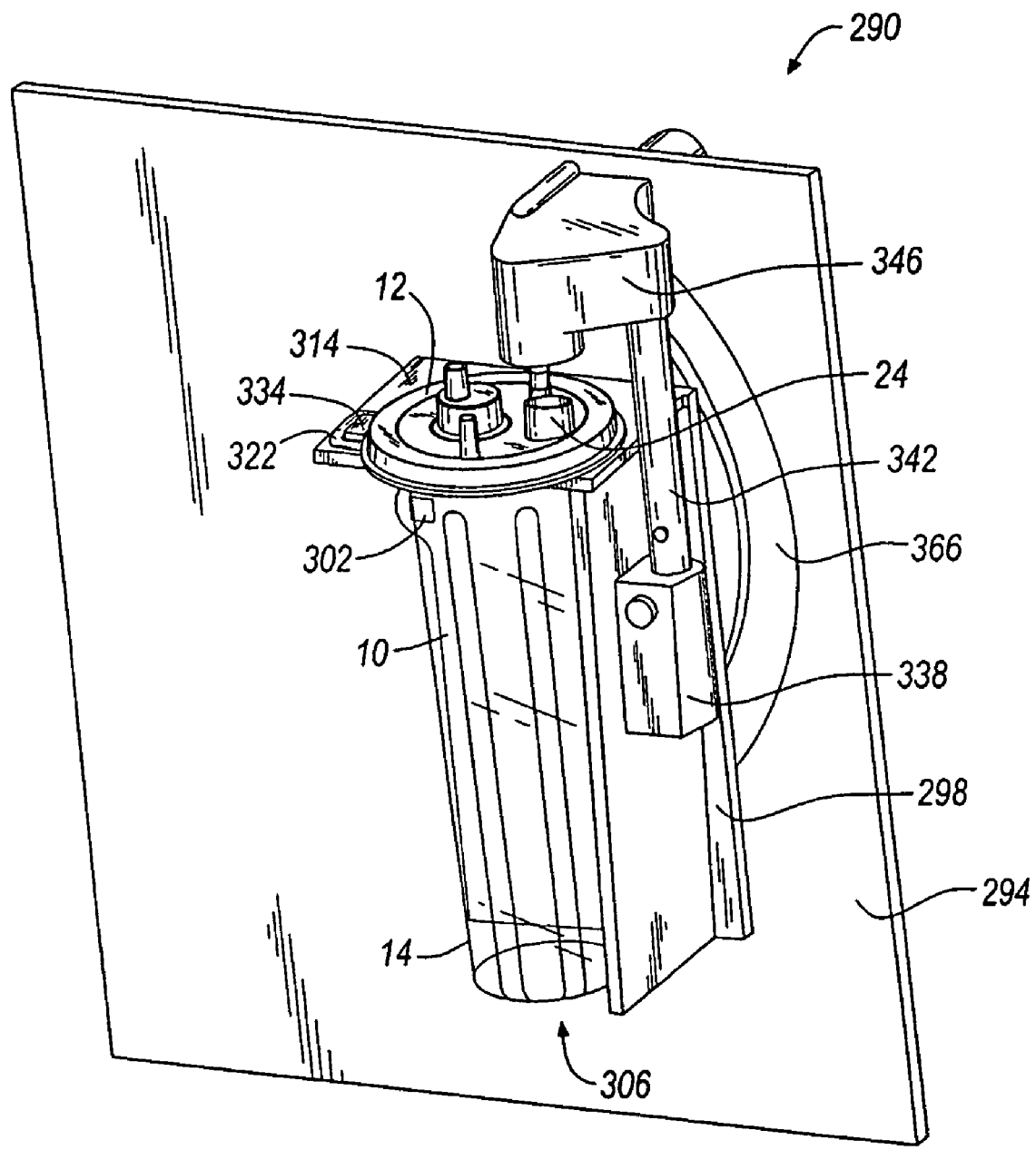
FIG. 13 is a perspective view of the apparatus in FIG. 12 with the liner-type medical suction apparatus.

The liner-type medical suction apparatus 10 includes an alignment member, such as a notch 322 to be aligned with a member 334 on the bracket 314 to properly position the liner-type medical suction apparatus 10 in the bracket 314 (illustrated in FIG. 13). Specifically, the notch 322 aligns the cover 12 of the liner-type medical suction apparatus 10 relative to the drainhead (discussed below). Alternatively, the bracket 314 includes the notch 322 and the liner-type medical suction apparatus 10 includes the member 334.

Referring to FIG. 12, the swingarm 298 includes a piston module 338, which supports a conduit 342. The conduit 342 is adapted to move vertically when activated by the piston module 338. The conduit 342 supports a drainhead 346 that moves vertically with the conduit 342 to interengage with the cover 12 of the liner-type medical suction apparatus 10. The piston module 338 can be spring-loaded and biased in an open position.

Figure 14:
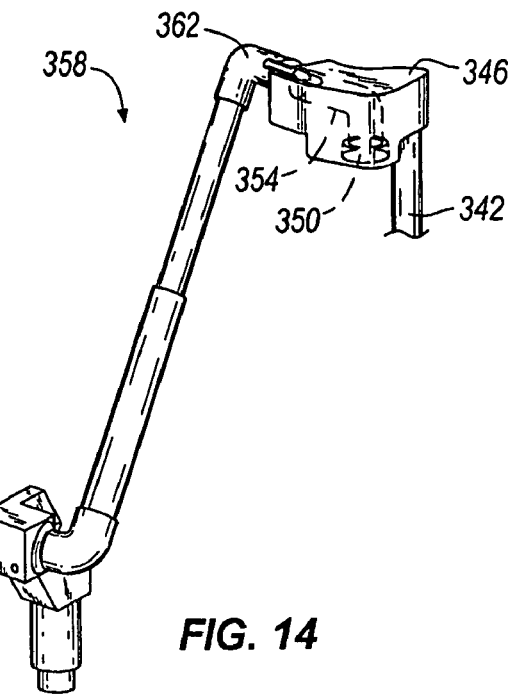
FIG. 14 is a perspective view of a drainhead and a plumbing system of the apparatus in FIG. 12.

As illustrated in FIG. 14, the drainhead 346 includes a drainage port 350 and a passageway 354 in fluid communication with the drainage port 350 and a plumbing system 358. The drainage port 350 in the drainhead 346 interengages with the open port 24 on the cover 12 of the liner-type medical suction apparatus 10 (illustrated in FIGS. 13 and 17). FIG. 13 illustrates the drainage device 290 with the liner-type medical suction apparatus 10, however, the drainage device 290 can also drain the rigid-walled suction apparatus 74.

Figure 15:
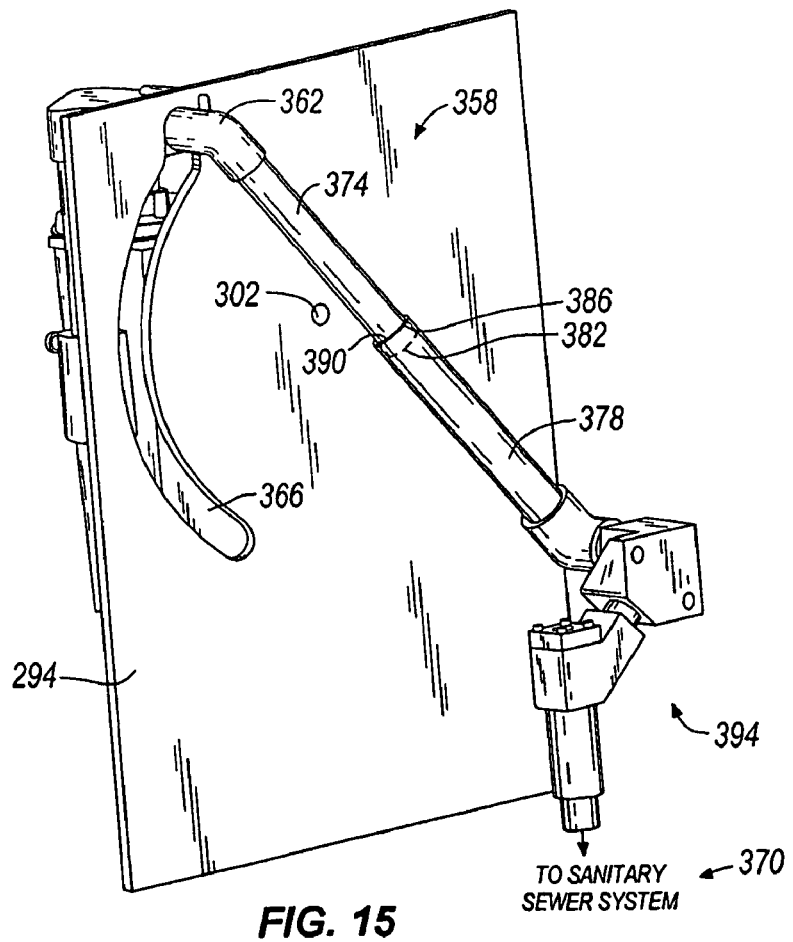
FIG. 15 is a back perspective view of the plumbing system of the apparatus in FIG. 12 with the liner-type medical suction apparatus.
Figure 16:
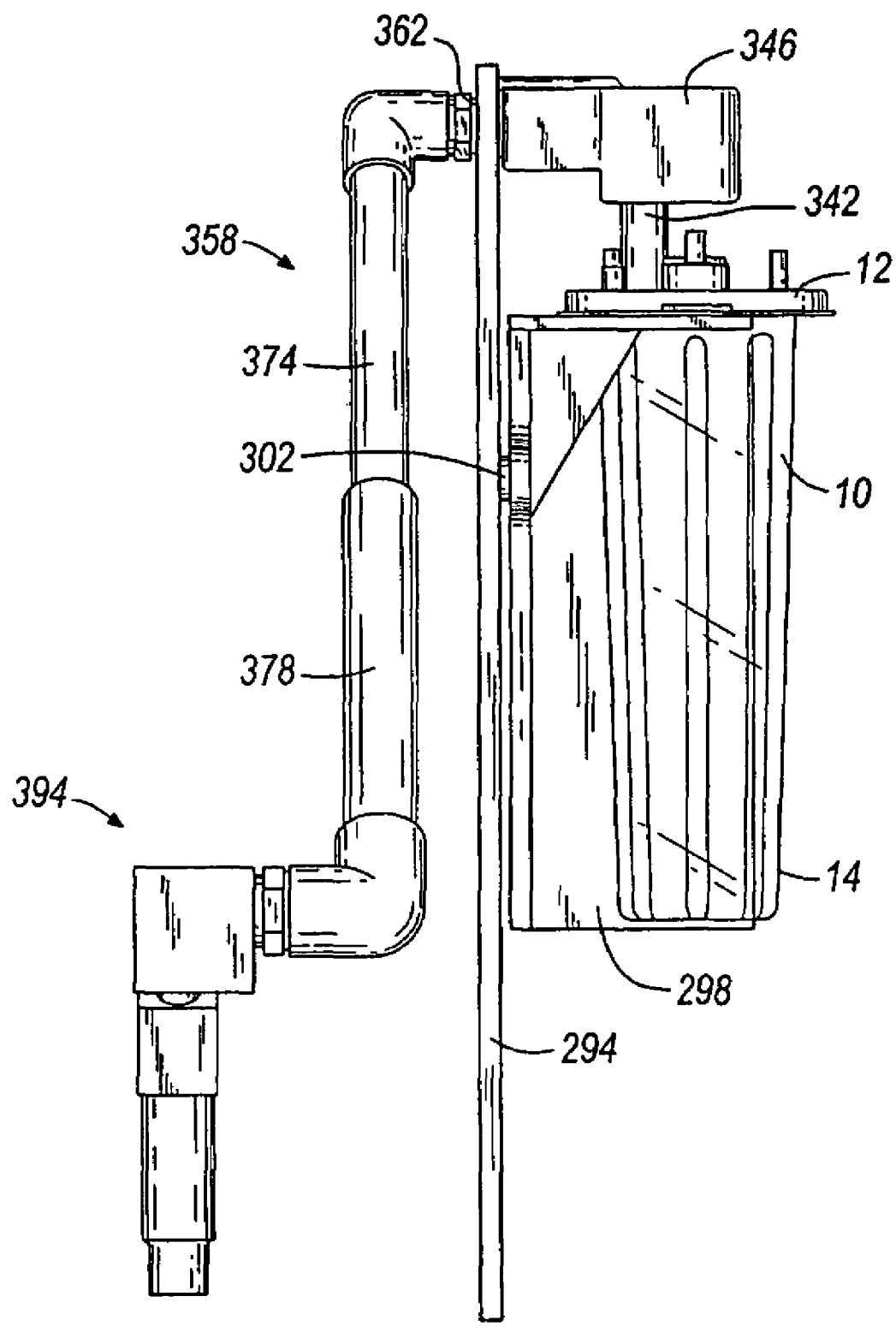
FIG. 16 is a side elevational view of the apparatus in FIG. 12 with the liner-type medical suction apparatus.

As best illustrated in FIG. 16, the drainhead 346 includes a conduit 362 that is connected to the plumbing system 358. The conduit 362 moves along a guide or pathway 366 (illustrated in FIGS. 12-15) formed in the housing 294 when the swingarm 298 is moved to pivot at pivot point 302.

Referring to FIG. 15, the housing 294 includes the plumbing system 358, which can be supported inside the housing 294, outside the housing 294 or partially inside and outside the housing 294. The plumbing system 358 connects to a sanitary sewer system 370. The plumbing system 358 includes a conduit 374 (or a plurality of conduits that are connectable to form conduit 374) connectable to the conduit 362 and a conduit 378. An end 382 of the conduit 374 is positioned within an end 386 having an opening 390 of the conduit 378 and slides/glides within the opening 390 of the conduit 378. The plumbing system 358 also includes a suction generator, such as a jet pump 394 connectable to the conduit 378 and the sanitary sewer system 370.

The drainage device 290 operates to drain the contents of the liner-type medical suction apparatus 10 in a manner in which there is minimal and preferably no contact with the liner contents. An operator positions the liner-type medical suction apparatus 10 in need of emptying or draining in the bracket 314 and aligns the notch 332 with the member 334 on the bracket 314 as illustrated in FIG. 13.

After the liner-type medical suction apparatus 10 is in position, the operator removes any caps from the open port 24 and activates the piston module 338, which automatically moves the drainhead 346 onto the cover 12 of the liner-type medical suction apparatus 10. In some embodiments, the operator manually moves the drainhead 346 onto the cover 12 of the liner-type medical suction apparatus 10. As the drainhead 346 moves vertically downward onto the cover 12, the conduit 362 travels in the pathway 366 for proper alignment with the open port 24 on the cover 12.

Figure 17:
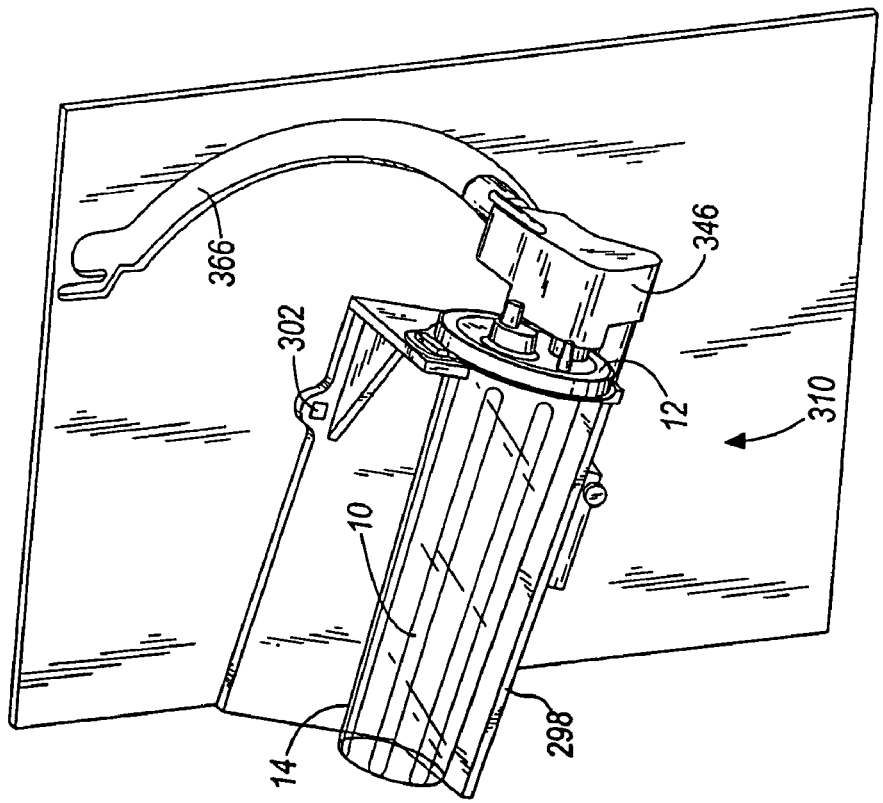
FIG. 17 is a perspective view of the apparatus in FIG. 12 with the liner-type medical suction apparatus.

When the drainhead 346 is properly seated on the cover 12 of the liner-type medical suction apparatus 10, a release lever and the jet pump 394 are activated (not necessarily, but could be a simultaneous activation), the swingarm 298 moves and the conduit 362 travels in the pathway 366 such that the liner-type medical suction apparatus 10 is transported from the first position 306 to the second position 310 as determined by the pathway 366 (illustrated in FIGS. 13 and 17). The operator does not need to manually move the swingarm 298, rather the swingarm 298 moves into the second position 310 under gravity and the weight of the contents in the liner-type medical suction apparatus 10. In some embodiments, the operator can manually move the swingarm 298 into the second position 310 as guided by the pathway 366. The swingarm 298 remains in the second position 310 by a lock mechanism.

Figure 18:
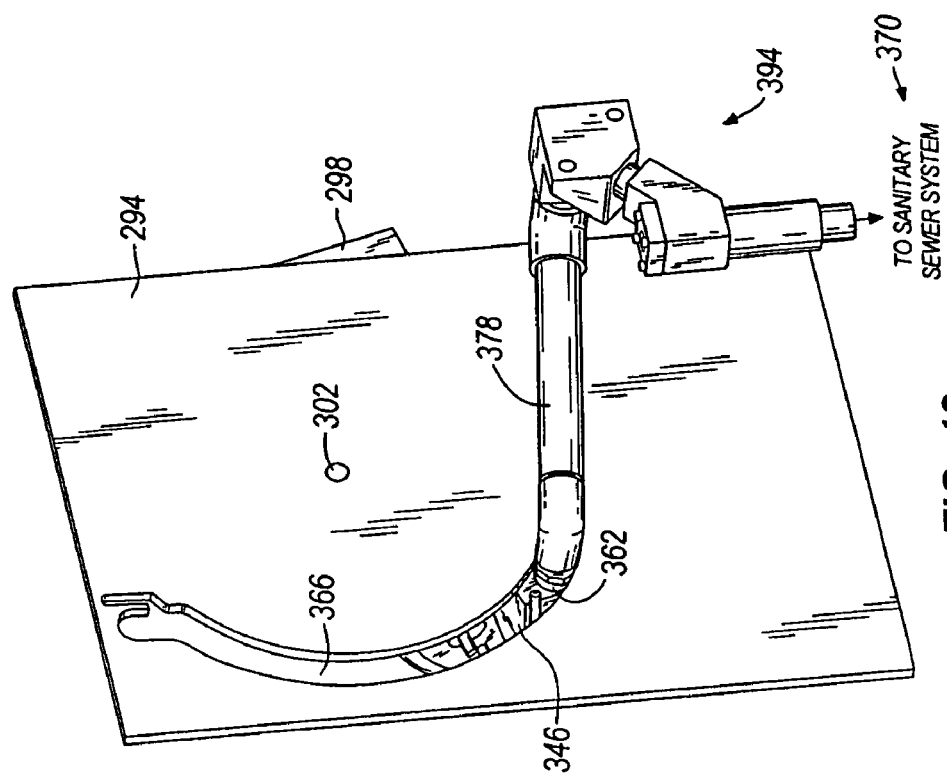
FIG. 18 is a back perspective view of the apparatus in FIG. 12.

As illustrated in FIGS. 15 and 18, as the swingarm 298 moves between the first position 306 and the second position 310, the conduit 374 slides into the conduit 378. With the swingarm 298 and the liner-type medical suction apparatus 10 in the second position 310, the contents in the liner-type medical suction apparatus 10 are drained by gravity and suctioned by the jet pump 394 through the drainage port 350, the passageway 354 in the drainhead 346, conduits 362, 374, and 378 to the sanitary sewer system 370. The swingarm 298 remains in the second position 310 until drainage of the liner-type medical suction apparatus 10 is completed.

After drainage of the liner-type medical suction apparatus 10 is completed, the operator disengages the lock mechanism, and the swingarm 298 and liner-type medical suction apparatus 10 are returned to the first position 306 by the operator. The operator activates the piston module 338, which automatically moves the drainhead 346 away from the cover 12 of the liner-type medical suction apparatus 10. In some embodiments, the operator manually moves the drainhead 346 away from the cover 12 of liner-type medical suction apparatus 10. The operator can then remove the liner-type medical suction apparatus 10 from the bracket 314 and dispose of the liner-type medical suction apparatus 10 into a white bag medical waste container.

Figure 19:
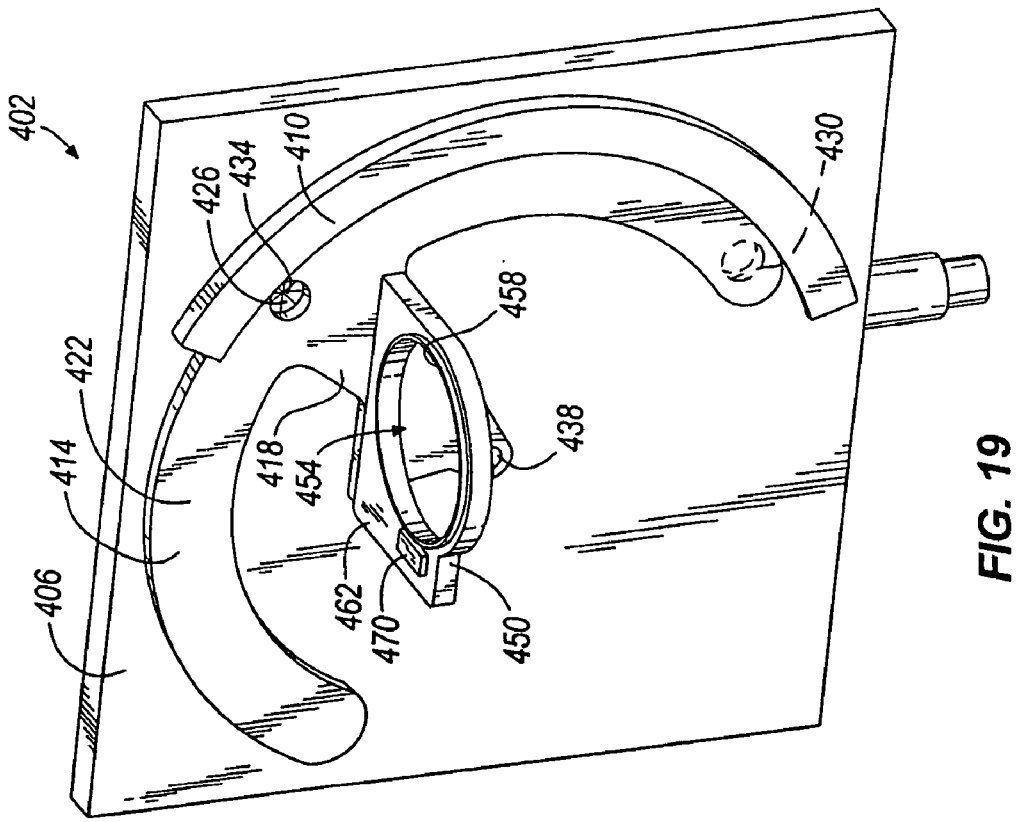
FIG. 19 is a perspective view of an apparatus and a method for draining a liner-type medical suction apparatus and a rigid-walled medical suction apparatus.

FIG. 19 illustrates a drainage device 402 that can be used to drain either the liner-type medical suction apparatus 10 or the rigid-walled suction apparatus 74. FIG. 19 illustrates the drainage device 402 with the liner-type medical suction apparatus 10, however, the drainage device 402 can also drain the rigid-walled suction apparatus 74.

The drainage device 402 can be positioned on the floor (i.e., freestanding) or mounted to a wall with hardware.

The drainage device 402 includes a housing 406, which supports a channel 410. The channel 410 guides and supports a swingarm 414 as illustrated in FIG. 19. The swingarm 414 can be a plate-like device with a central portion 418 and a C-shaped portion 422. The C-shaped portion 422 includes an opening 426, which aligns with an opening 430 in the housing 406. The opening 426 includes a closure device 434, such as a dynamic seal, a valve, flap, and like devices. The closure device 434 prevents the contents of the liner-type medical suction apparatus 10 from leaking out of the drainhead (discussed below) until the opening 426 in the swingarm 414 is aligned with the opening 430 in the housing 406. Alternatively, the closure device 434 can be positioned in the opening 430 of the housing 406. The central portion 418 of the swingarm 414 is pivotably mounted to the housing 406 through a shaft at pivot point 438 (shown in FIG. 19). The swingarm 414 is pivotably movable between a first position 442 (illustrated in FIG. 20) and a second position 446 (illustrated in FIG. 22).

In some embodiments of the invention, the second position 446 is in the range of about 90 degrees to about 180 degrees, and more particularly in the range of about 100 degrees to about 140 degrees, and most preferably about 135 degrees, from the first position 442. The swingarm 414 pivots in a clockwise direction when moved between the first position 442 and the second position 446. Likewise, the swingarm 414 rotates in a counter-clockwise direction when moved between the second position 446 and the first position 442. However, movement of the swingarm 414 can vary in type of motion and direction.

The swingarm 414 includes a support member, such as a bracket 450. The bracket 450 can support a flange 458, which is adapted to support the liner-type medical suction apparatus 10. In some embodiments, the flange 458 is removable such that the bracket 450 is adapted to support various sizes of liner-type medical suction apparatuses 10. In other embodiments, the bracket 450 is adapted to support various sized flanges 458, which can be exchangeable depending on the size of the liner-type medical suction apparatus 10. The bracket 450 includes an opening 454 adapted to receive the liner-type medical suction apparatus 10. The bracket 450 can include a handle 462.

Figure 20:
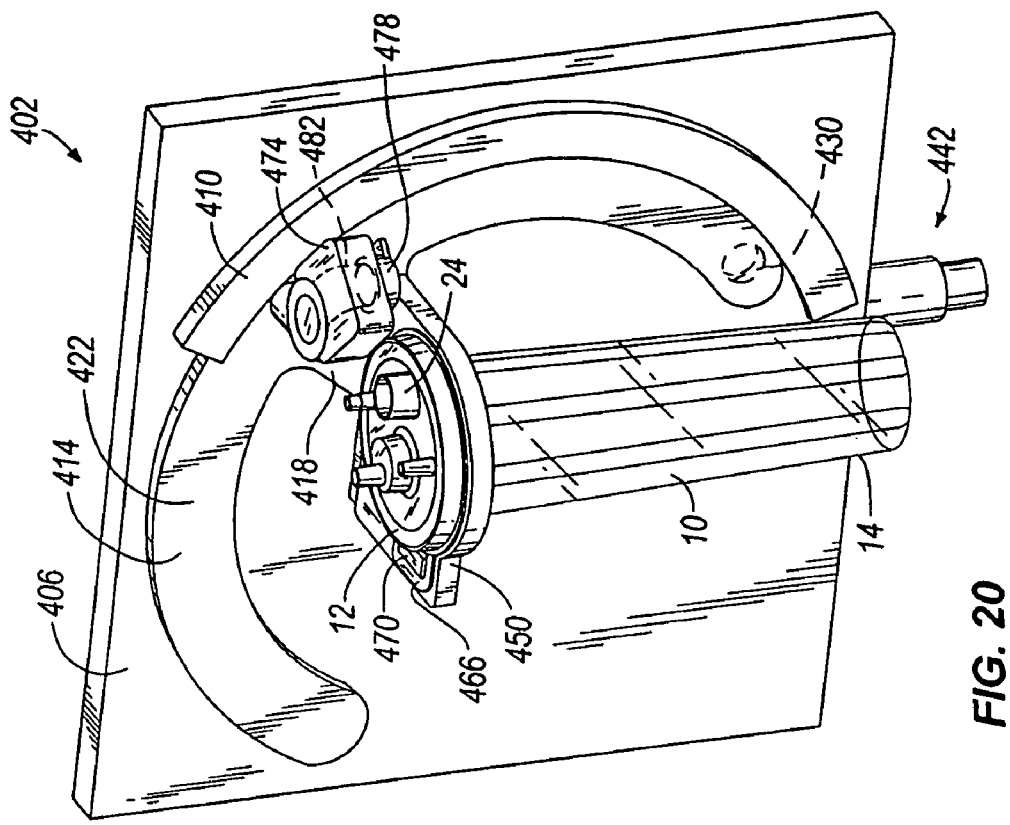
FIG. 20 is a perspective view of the apparatus in FIG. 19 with the liner-type medical suction apparatus.

The liner-type medical suction apparatus 10 includes an alignment member, such as a notch 466 to be aligned with a member 470 on the bracket 450 to properly position the liner-type medical suction apparatus 10 in the bracket 450 (illustrated in FIG. 20). Specifically, the notch 466 aligns the cover 12 of the liner-type medical suction apparatus 10 relative to the drainhead (discussed below). Alternatively, the bracket 450 includes the notch 466 and the liner-type medical suction apparatus 10 includes the member 470.

As illustrated in FIG. 20, the drainage device 402 includes a drainhead 474, which includes a drainage port 478 and a passageway 482 in fluid communication with the drainage port 478 and the opening 426 in the swingarm 414. The drainage port 478 in the drainhead 474 interengages with the open port 24 on the cover 12 of liner-type medical suction apparatus 10 (illustrated in FIGS. 21-22). The drainhead 474 can pivot onto the open port 24. The drainhead 474 can also be configured to be spring-biased in the open position and manually moved onto the open port 24. The drainhead 474 can be further configured to align with the open port 24 in any suitable manner.

Figure 21:
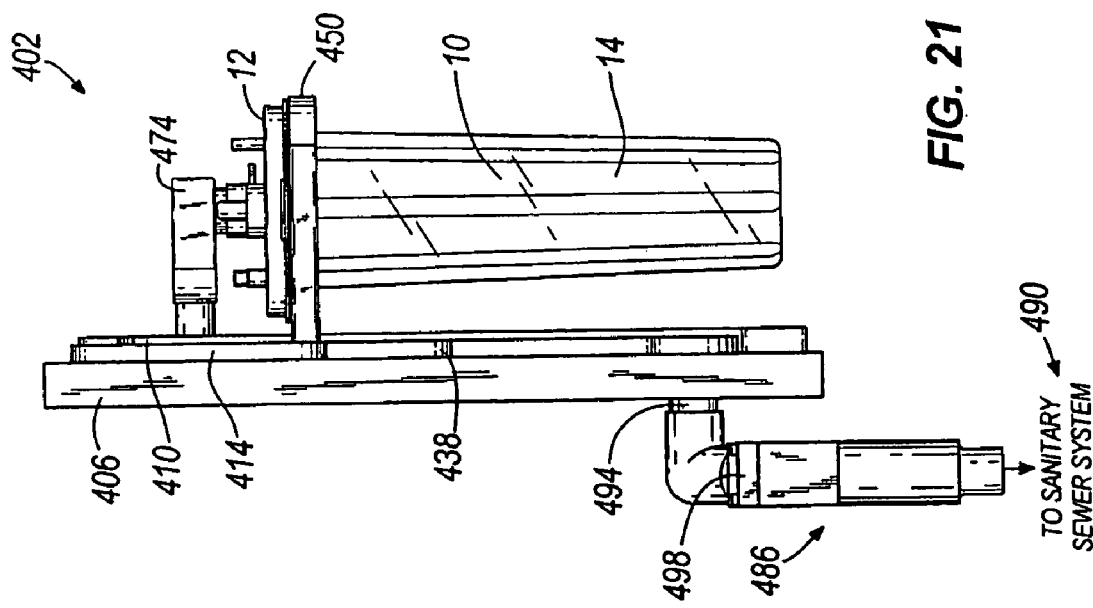
FIG. 21 is a side elevational view of the apparatus in FIG. 19 with the liner-type medical suction apparatus.

Referring to FIG. 21, the housing 406 includes a plumbing system 486, which can be supported inside the housing 406, outside the housing 406 or partially inside and outside the housing 406. The plumbing system 486 connects to a sanitary sewer system 490. The plumbing system 486 includes a conduit 494 (or a plurality of conduits that are connectable to form conduit 494) in fluid communication with the opening 430 in the housing 406. The plumbing system 486 also includes a suction generator, such as a jet pump 498 connectable to the conduit 494 and the sanitary sewer system 490 (through additional conduits).

The drainage device 402 operates to drain the contents of the liner-type medical suction apparatus 10 in a manner in which there is minimal and preferably no contact with the liner-type medical suction apparatus 10 contents. An operator positions the liner-type medical suction apparatus 10 in need of emptying or draining in the bracket 450 and aligns the notch 466 on the liner-type medical suction apparatus 10 with the member 470 in the bracket 450 as illustrated in FIG. 20.

After the liner-type medical suction apparatus 10 is in position, the operator removes any caps from the open port 24 on the cover 12 and activates the drainhead 474 to automatically move into contact with the cover 12 of the liner-type medical suction apparatus 10. In some embodiments, the operator manually moves the drainhead onto the cover 12 of the liner-type medical suction apparatus 10. The drainhead 474 moves vertically downward onto the cover 12 to align the drainage port 478 and be in fluid communication with the open port 24 on the cover 12.

Figure 22:
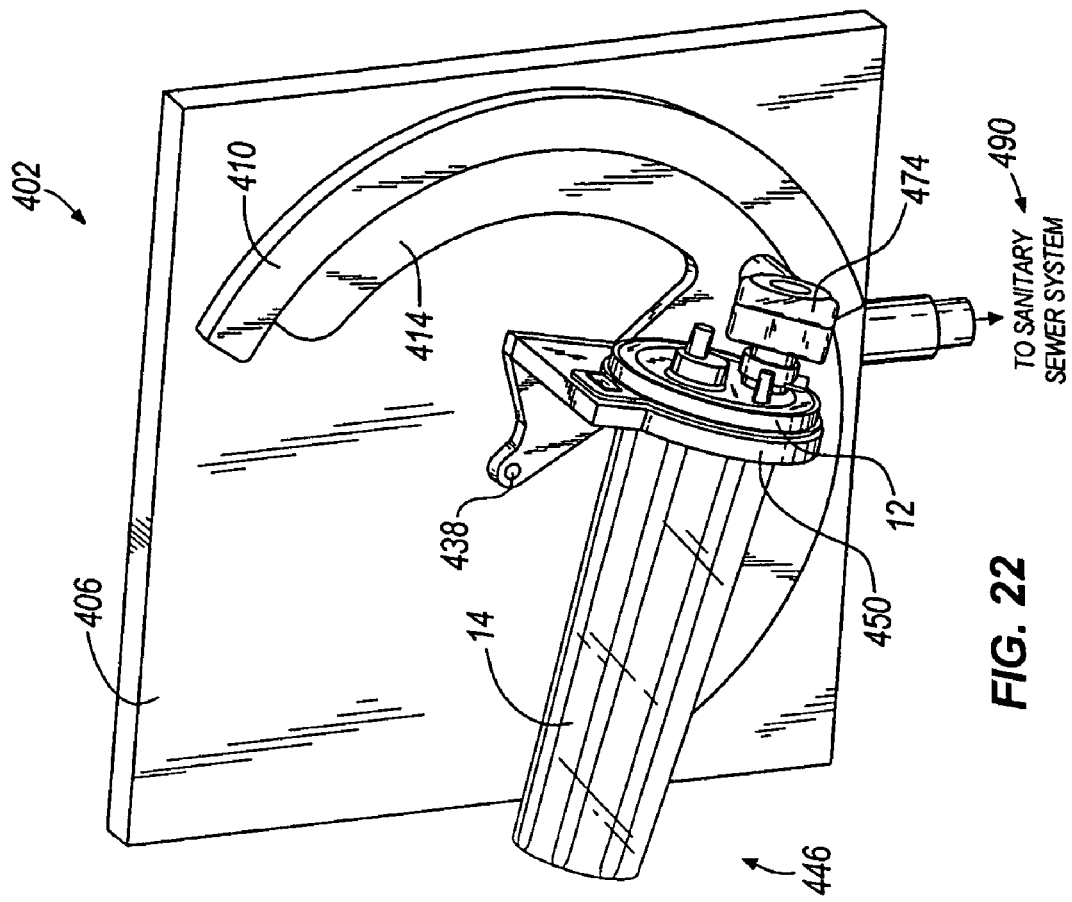
FIG. 22 is a perspective view of the apparatus in FIG. 19 with the liner-type medical suction apparatus.

When the drainhead 474 is properly seated on the cover 12, a release and the jet pump 498 are activated (not necessarily, but could be a simultaneous activation), the swingarm 414 travels in a clockwise path such that the liner-type medical suction apparatus 10 is transported from the first position 442 to the second position 446 (illustrated in FIGS. 20 and 22). The operator does not need to manually move the swingarm 414, rather the swingarm 414 moves into the second position 446 under gravity and the weight of the contents in the liner-type medical suction apparatus 10. In some embodiments, the operator can manually move the swingarm 414 into the second position 446. The swingarm 414 remains in the second position 446 by a lock.

With the swingarm 414 and the liner-type medical suction apparatus 10 in the second position 446, the contents in the liner-type medical suction apparatus 10 are drained by gravity and suctioned by the jet pump 498 through the drainage port 478, the passageway 482 in the drainhead 474, openings 426 and 430, conduit 494 to the sanitary sewer system 490. The swingarm 414 remains in the second position 446 until drainage of the liner-type medical suction apparatus 10 is completed.

After drainage of the liner-type medical suction apparatus 10 is completed, the operator disengages the lock mechanism, and the swingarm 414 and liner-type medical suction apparatus 10 are returned to the first position 442. The operator activates the drainhead 474, which automatically moves the drainhead 474 away from the cover 12 of the liner-type medical suction apparatus 10. In some embodiments, the operator manually moves the drainhead 474 away from the cover 12 of liner-type medical suction apparatus 10. The operator can then remove the liner-type medical suction apparatus 10 from the bracket 450 and dispose of the liner-type medical suction apparatus 10 into a white bag medical waste container.

Various features and advantages of the invention are set forth in the following claims.

What is claimed is:

1. A medical device for draining either a liner-type suction canister or a rigid walled suction canister, both having a cover having therein a port and both containing fluid to be drained, said device comprising:
   a housing in communication with a sanitary sewer line;
   a swingarm coupled to and pivotable with respect to the housing;
   a drainhead coupled to and pivotable with respect to the swingarm, the drainhead having a passageway therein, the drainhead having a first position not engageable with a liner-type and a rigid-walled suction canister and a second position engageable with the liner-type and the rigid walled suction canister, and in its second position, the passageway being adapted to be in fluid communication with the port in the cover;
   a support member directly connected to the swingarm for supporting the liner-type and the rigid-walled suction canister; and
   a suction source in communication with the passageway and adapted to drain the fluid contained in the liner-type and the rigid-walled suction canister to a sanitary sewer.

2. The medical device of claim 1 wherein the support member includes an alignment member adapted to align both the liner type and the rigid walled suction canister relative to the drainhead.

3. The medical device of claim 1 wherein the swingarm is movable between a first position and a second position.

4. The medical device of claim 3 wherein the suction source is activated when the swingarm is in its second position.

5. The medical device of claim 3 wherein the drainhead includes a latch, wherein when the drainhead is in its second position, the latch engages the swingarm to positionally fix the drainhead relative to the swingarm.

6. The medical device of claim 3 wherein the swingarm includes a lock, and wherein the latch engages the lock to positionally fix the drainhead relative to the swingarm.

7. The medical device of claim 3 wherein the swingarm includes a handle to enable rotation of the swingarm.

8. The medical device of claim 1 wherein the suction source includes a jet pump.

9. A medical device for draining fluid contained in either a liner-type or a rigid-walled suction canister, said device comprising:
   a movable swingarm;
   a support member directly connected to the swingarm, the support member adapted to support either a liner-type or a rigid-walled suction canister, the swingarm adapted to move the canister between a first position and a second position; and
   a drainhead having a passageway therein, the drainhead adapted to engage the liner-type and the rigid-walled suction canister to enable fluid communication between the fluid contained in the liner-type and the rigid-walled suction canister and a sewer line.

10. The medical device of claim 9 and further comprising a suction source in communication with the passageway for draining fluid contained in the liner-type and the rigid-walled suction canister.

11. A medical device for draining fluid contained in a liner-type or a rigid walled suction canister, and having a cover, said device comprising:
    a housing;
    a swingarm coupled to the housing and adapted to support either a liner-type or a rigid-walled suction canister, the swingarm adapted to move the canister between a first position and a second position; and
    one of a first drainhead coupled to the swingarm and adapted to engage a cover of the liner-type suction canister and a second drainhead coupled to the swingarm and adapted to engage a cover of the rigid-walled suction canister, the first and second drainheads having therein a passageway such that fluid is drained from the liner-type and the rigid-walled suction canister through the passageway and into the housing when the swingarm is in its second position.

12. The medical device of claim 11 wherein the first and second drainheads are interchangeably mountable to a shaft on the housing.

13. The medical device of claim 11 wherein the first and second drainheads are mountable to a shaft on the housing.

14. The medical device of claim 13 wherein the first and second drainheads are interchangeably mountable to a shaft on the housing.

15. A method for draining either a liner-type or a rigid-walled suction canister filled with fluid using one device, said method comprising:
    positioning either a liner-type or a rigid-walled suction canister on a swingarm;
    coupling a drainhead on a device to a cover of one of the liner-type suction canister and the rigid-walled suction canister;
    rotating the canister with the swingarm; and
    activating a suction source to drain the fluid from one of the liner-type suction canister and the rigid-walled suction canister through the drainhead to a sanitary sewer.

16. A method for draining a liner-type or a rigid-walled suction canister, and having a cover, filled with fluid using one device, said method comprising:
    placing one of the liner-type suction canister and the rigid-walled suction canister in communication with a device;
    pivoting a drainhead on the device to establish fluid communication between the drainhead and a port on a cover of one of the liner-type suction canister and the rigid-walled suction canister; and
    activating a suction source to drain the fluid from the selected one of the liner-type suction canister and the rigid-walled suction canister through the drainhead to a sanitary sewer.

17. A method for draining either a liner-type or a rigid-walled suction canister filled with fluid using one device, said method comprising:
    selecting one of the liner-type suction canister and the rigid walled suction canister to be drained;
    selecting a first drainhead if the liner-type suction canister is to be drained;
    selecting a second drainhead if the rigid-walled suction canister is to be drained;
    moving the selected drainhead and the selected suction canister relative to one another to establish fluid communication between a port on a cover of the selected suction canister and the selected drainhead;
    moving the selected drainhead and the selected suction canister from a first position to a second position; and
    activating a suction source to drain the fluid from the selected suction canister, through the selected drainhead, and to a sanitary sewer.

18. The method of claim 17 wherein the first and second drainheads are interchangeably mounted to a shaft.

19. The method of claim 17 wherein the step of selecting a first drainhead includes mounting the first drainhead to a shaft.

20. The method of claim 17 wherein the step of selecting a second drainhead including mounting the second drainhead to a shaft.

* * * * *

UNITED STATES PATENT AND TRADEMARK OFFICE
CERTIFICATE OF CORRECTION

PATENT NO. : 7,585,292 B2 Page 1 of 1
APPLICATION NO. : 10/834594
DATED : September 8, 2009
INVENTOR(S) : Barry G. Anderson et al.

It is certified that error appears in the above-identified patent and that said Letters Patent is hereby corrected as shown below:

On the Title Page of the patent at (63), add --Continuation of application No. 09/819,243, filed on March 28, 2001, now U.S. Patent No. 6,626,877--

Signed and Sealed this

Fourth Day of May, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,585,292 B2 | Page 1 of 1 |
| APPLICATION NO. | : 10/834594 | |
| DATED | : September 8, 2009 | |
| INVENTOR(S) | : Anderson et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 989 days.

Signed and Sealed this

Fourteenth Day of September, 2010

David J. Kappos
*Director of the United States Patent and Trademark Office*